(12) United States Patent
Ahn et al.

(10) Patent No.: US 8,178,697 B2
(45) Date of Patent: May 15, 2012

(54) METHOD FOR THE PREPARATION OF ATORVASTATIN AND INTERMEDIATES USED THEREIN

(75) Inventors: Soon Kil Ahn, Seoul (KR); Hong-Woo Lee, Ansan-si (KR); Choong Leol Yoo, Incheon (KR); Young-Min Kim, Seoul (KR); Chang Geun Song, Cheonan-si (KR); Sung Kwun Kang, Cheonan-si (KR); Jun A. You, Hwaseong-si (KR); Bong Kwan Soh, Cheonan-si (JP); Dong Hyuk Nam, Seoul (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 12/864,139

(22) PCT Filed: Apr. 25, 2008

(86) PCT No.: PCT/KR2008/002373

§ 371 (c)(1),
(2), (4) Date: Oct. 6, 2010

(87) PCT Pub. No.: WO2009/093776

PCT Pub. Date: Jul. 30, 2009

(65) Prior Publication Data

US 2011/0015407 A1    Jan. 20, 2011

(30) Foreign Application Priority Data

Jan. 25, 2008  (KR) .......................... 10-2008-0007757

(51) Int. Cl.
*C07F 5/02* (2006.01)
*C07D 207/335* (2006.01)

(52) U.S. Cl. ....................................... 548/405; 548/537

(58) Field of Classification Search ........................ None
See application file for complete search history.

(56) References Cited

FOREIGN PATENT DOCUMENTS

| WO | 2002043667 A2 | 6/2002 |
|---|---|---|
| WO | 2005118536 A1 | 12/2005 |
| WO | 2006032959 A2 | 3/2006 |
| WO | 2007028412 A1 | 3/2007 |
| WO | 2007029216 A1 | 3/2007 |
| WO | 2006097909 A1 | 9/2007 |
| WO | 2007099552 A2 | 9/2007 |

OTHER PUBLICATIONS

Roth, et al.; "Inhibitors of Cholesterol Biosynthesis. 3. Tetrahydro-4-hydroxy 6 [2-(1H pyrrol-1-yl)ethyl]-2H-pyran-2-one Inhibitors of HMG-CoA Reductase. 2. Effects of Introducing Substituents at Positions Three and Four of the Pyrrole Nucleus," Journal of Medicinal Chemistry, 1991, vol. 34, No. 1, pp. 357-366.
International Search Report dated Oct. 6, 2008 for PCT/KR2008/002373.

*Primary Examiner* — Sun Jae Loewe
(74) *Attorney, Agent, or Firm* — Heslin Rothenberg Farley & Mesiti P.C.

(57) ABSTRACT

The present invention relates to a novel method for preparing atorvastatin. According to the present invention, provided are a novel intermediate of the preparation of atorvastatin and a method of preparing large amounts of atorvastatin in a safe manner using the intermediate.

3 Claims, No Drawings

METHOD FOR THE PREPARATION OF ATORVASTATIN AND INTERMEDIATES USED THEREIN

CROSS REFERENCE TO RELATED APPLICATION

This application is the National Phase filing of International Application No. PCT/KR2008/002373, filed Apr. 25, 2008, which claims priority to Korean Application No. 10-2008-0007757, filed Jan. 25, 2008. The entire content of each prior application is hereby incorporated by reference.

TECHNICAL FIELD

The present invention relates to a method for preparing atorvastatin. More specifically, the present invention relates to a novel intermediate for the preparation of atorvastatin and a method of preparing atorvastatin using the same.

BACKGROUND ART

Drugs, which show cholesterol lowering effects through a mechanism of inhibiting the activity of 3-hydroxy-3-methyl-glutaryl coenzyme A reductase (HMG-CoA reductase), are generally called "statin". Among them, the first generation compounds, developed earliest, include simvastatin, lovastatin, pravastatin and the like, which are fermentation products, and the second generation compounds, which are synthetic drugs, include atorvastatin, fluvastatin, rosuvastatin, pitavastatin and the like.

Among them, atorvastatin is a very promising compound, which showed the highest growth rate during the recent three years and had a market size of 13.2 billion dollars in the year 2006. Also, the annual average growth rate was more than 20%.

International Patent Publication No. WO 89/07598, assigned to Warner-Lambert Company commercially producing atorvastatin, discloses a process for the preparation of atorvastatin. In this patent, as can be seen in the following reaction scheme (1), a 1,4-dione compound represented by formula A is allowed to react with a chiral intermediate represented by formula B, to obtain a compound represented by formula C, which is then converted to atorvastatin:

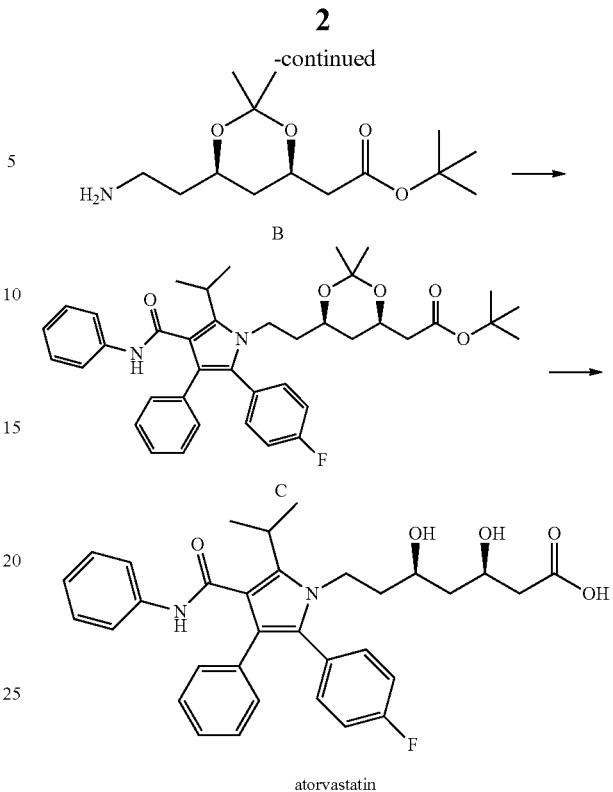

In the reaction scheme 1, the first reaction comprises refluxing the compound of formula A and the compound of formula B in a hydrocarbon solvent, such as toluene, cyclohexane or a mixture thereof, and allowing the resulting compound of formula C into contact with aqueous acid solution such as aqueous hydrochloric acid solution.

However, the preparation process according to the reaction scheme 1 has problems in that the reaction time in the first reaction is very long (about 100 hours), leading to an increase in side reactions, and the total yield of the product is as very low as about 15%, because it is not easy to remove produced byproducts.

International Patent Publication No. WO 02/057274 discloses a process for preparing atorvastatin, in which, as shown in the following reaction scheme 2, a compound of formula (A) and a compound of formula (D) are allowed to reflux and condensate by using acetic acid in a xylene solvent to prepare a compound of formula (E), which is then hydrolyzed, thus preparing atorvastatin.

[Reaction Scheme 1]

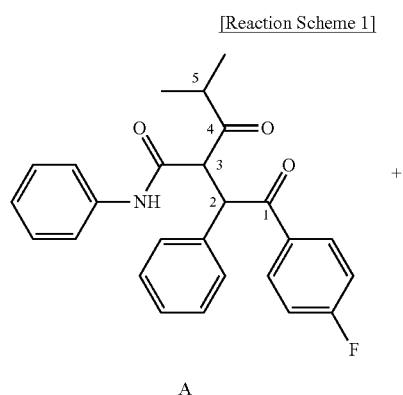

[Reaction Scheme 2]

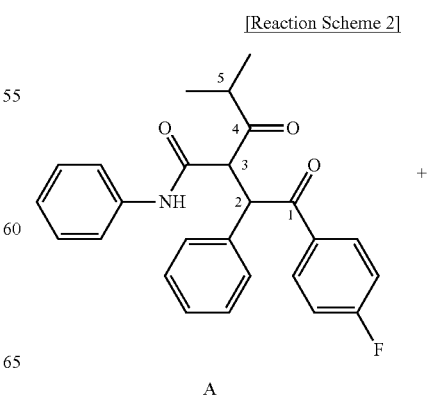

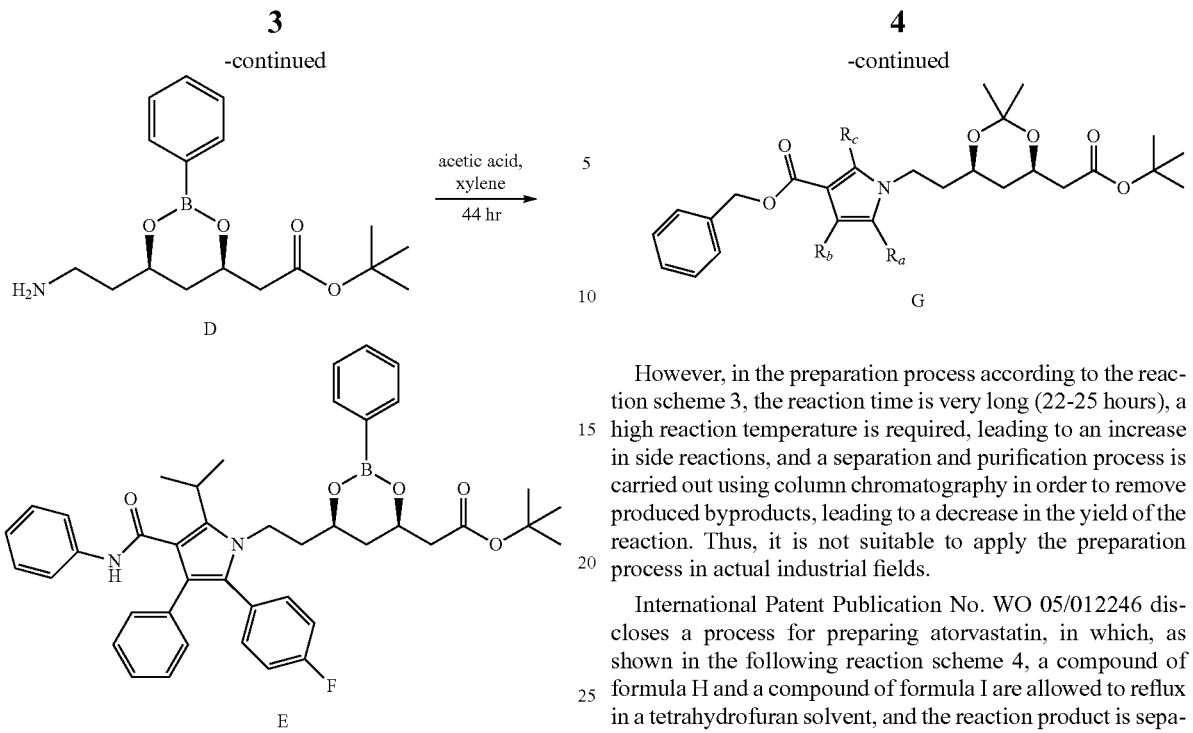

However, in the preparation process according to the reaction scheme 2, the reaction time is very long (about 44 hours) and, in addition, intensive reaction conditions are required, because the reaction must be carried out at high temperature (not less than 110° C.) using xylene, having a high boiling point, as a reaction solvent. Also, it is difficult to remove the remaining solvent, the toxicity of the solvent itself can cause a serious problem in terms of the safety of workers, and thus it is unsuitable to apply the preparation process in actual industrial fields. In addition, there are problems in that the production of byproducts increases due to a very long reaction time and that it is not easy to remove byproducts.

International Patent Publication No. WO 04/106299 discloses a process for preparing atorvastatin, in which, as shown in the following reaction scheme 3, a compound of formula F and a compound of formula B are allowed to reflux and condensate by using pivalic acid in a mixed solvent of heptane, toluene and tetrahydrofuran.

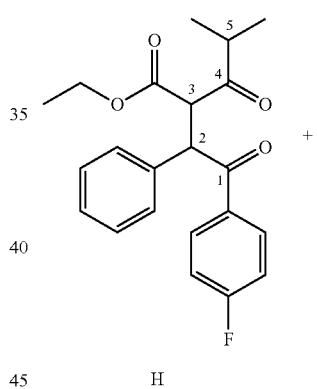

However, in the preparation process according to the reaction scheme 3, the reaction time is very long (22-25 hours), a high reaction temperature is required, leading to an increase in side reactions, and a separation and purification process is carried out using column chromatography in order to remove produced byproducts, leading to a decrease in the yield of the reaction. Thus, it is not suitable to apply the preparation process in actual industrial fields.

International Patent Publication No. WO 05/012246 discloses a process for preparing atorvastatin, in which, as shown in the following reaction scheme 4, a compound of formula H and a compound of formula I are allowed to reflux in a tetrahydrofuran solvent, and the reaction product is separated and purified using column chromatography:

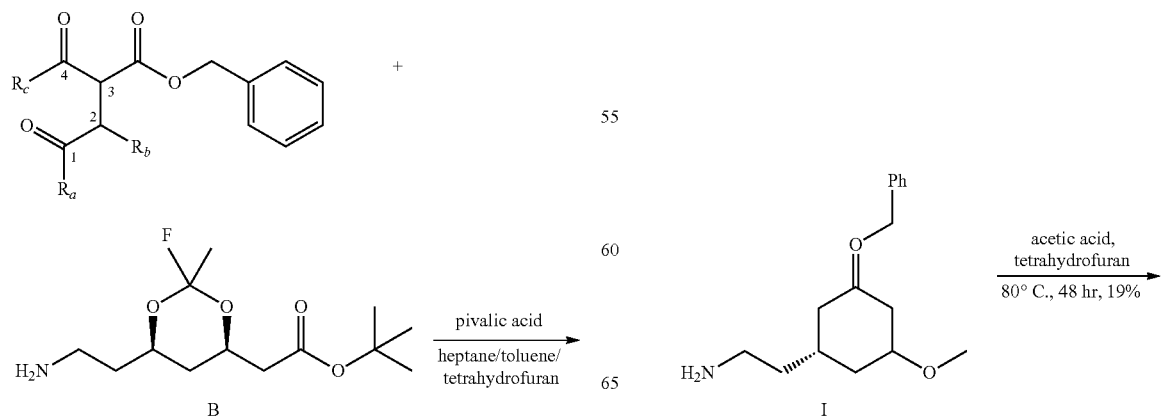

-continued

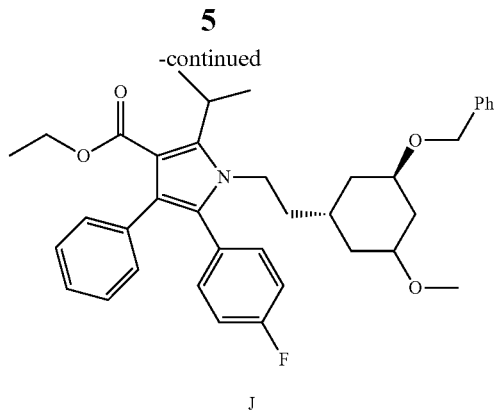

J

Unlike the 1,4-dione compound disclosed in International Patent Publication No. WO 89/07598, the 1,4-dione compound of formula H shown in the reaction scheme 4 has a structure very similar to a 1,4-dione compound, which is used in the present invention. However, similarly to the preparation process disclosed in International Patent Publication No. WO 89/07598, the preparation process according to the reaction scheme 4 is difficult to apply in actual industrial fields, because the reaction time is very long (about 2 days) and, in addition, the yield of the product is as very low as about 19%.

Also, preparation processes, disclosed in U.S. Pat. Nos. 4,647,576 and 4,681,893, have problems in that optically pure products cannot be produced and, even though the products can be separated into pure products, the separation and purification process is very expensive. In addition, there are problems in that the reaction time is long, and not less than 50% of the starting material is lost, leading to a decrease in the yield of the reaction.

The reason for the results (long reaction time and low yield) of the prior preparation processes as described above is that a substituent group (e.g., an amide or ester compound) is present at carbon location 3 of the reactant 1,4-dione compound (formula A, F or H), and thus, during the reaction, a structural arrangement resulting from the steric hindrance of carbon locations 2 and 3 in the molecule of the 1,4-dione compound inhibits a cyclization reaction with the chiral intermediate (formula B, D or I), resulting in a decrease in the total reaction yield (J. Med. Chem., 1991, 34, 357~366).

DISCLOSURE OF INVENTION

Technical Problem

The present inventors have conducted many studies to a method for preparing atorvastatin, which can overcome the above-described problems occurring in the prior art, and, as a result, have synthesized a novel intermediate (formula 7a) using a 1,4-dione compound (formula 5), which contains no a substituent group at carbon location 3 and has a structural arrangement, which can be easily cyclized with a chiral intermediate, and have developed a method of preparing atorvastatin or a pharmaceutically acceptable salt thereof by using the intermediate in high efficiency and high yield, thereby completing the present invention.

Technical Solution

The present invention relates to a novel method for preparing atorvastatin and provides a method for preparing a compound of the following formula 1 or a pharmaceutically acceptable salt thereof, which comprises the steps of:

(1) reacting a compound of the following formula 7 with a compound of the following formula 8 to obtain a compound of the following formula 9, and (2) deprotecting and hydrolyzing the compound of formula 9:

[Formula 1]

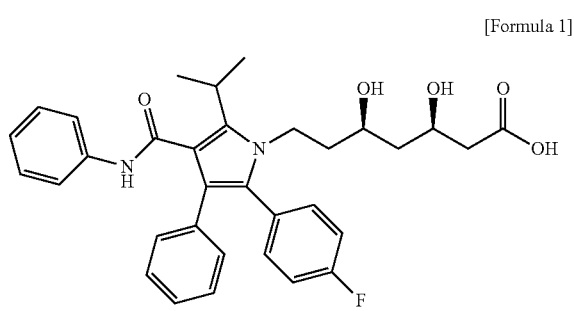

[Formula 7]

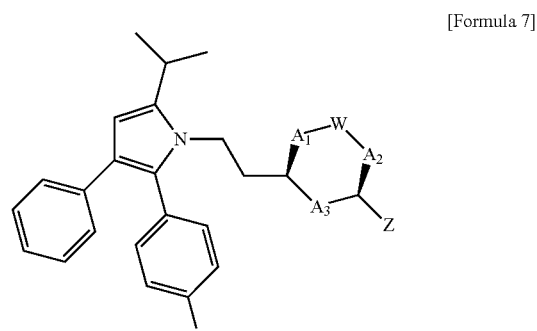

[Formula 8]

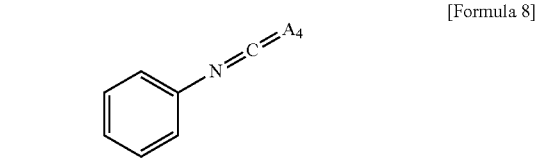

[Formula 9]

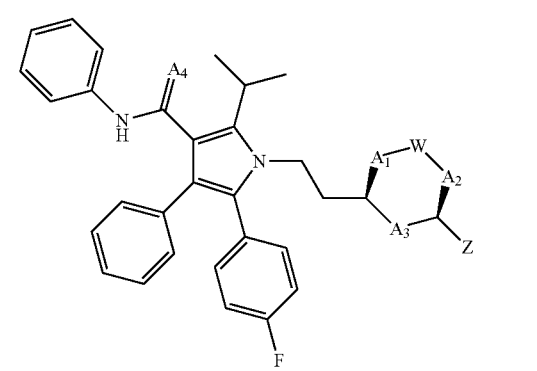

wherein $A_1$, $A_2$ and $A_3$ are each independently $CH_2$ or oxygen;

W is

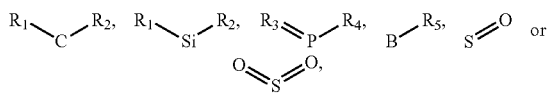

wherein $R_1$ and $R_2$ are each independently hydrogen, OH, a straight or branched chain alkyl having 1-8 carbon atoms, phenyl or

wherein $R_6$ is hydrogen, methyl, ethyl, tetrahydropyranyl, benzyl, trialkylsilyl or triarylsilyl, or $R_1$ and $R_2$ together form oxygen (=O) or —$(CH_1)_n$—, wherein n is 4 or 5, $R_3$ is oxygen or sulfur, $R_4$ is Cl, Br, F, I, a straight or branched chain alkyl having 1-8 carbon atoms, phenyl, trityl, OH, an alkoxy having 1-8 carbon atoms, or phenoxy, and $R_5$ is oxygen (=O), a straight or branched chain alkyl having 1-8 carbon atoms, an alkoxy having 1-8 carbon atoms, an aryl or aryloxy, wherein an aryl or aryloxy is unsubstituted or substituted with an alkyl having 1-4 carbon atoms, an alkoxy having 1-4 carbon atoms, nitro or halogen, or a $C_6$-$C_{10}$ heteroaryl comprising one or two heteroatoms selected from a group consisting of N, O and S; and Z is oxygen (=O),

wherein $R_7$ is hydrogen, methyl, ethyl or acetyl, or —$CH_2COR_8$, wherein $R_8$ is

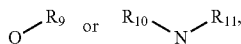

$R_9$ is hydrogen, a straight or branched chain alkyl having 1-8 carbon atoms, a cycloalkyl group having 3-6 carbon atoms, phenyl, benzyl or α,α-dimethylbenzyl, and $R_{10}$ and $R_{11}$ are each independently hydrogen, a straight or branched chain alkyl having 1-8 carbon atoms, a cycloalkyl group having 3-6 carbon atoms, benzyl or phenyl, or $R_{10}$ and $R_{11}$ together form —$(CH_2)_4$—, —$(CH_2)_5$—, —$(CH(R_{12})CH_2)_3$—, —$(CH(R_{12})CH_2)_4$—, —$(CH(R_{12})(CH_2)_2CH(R_{12}))$—, —$(CH(R_{12})(CH_2)_3CH(R_{12}))$—, —$CH_2CH_2$—O—$CH_2CH_2$—, —$CH(R_{12})CH_2$—O—$CH_2CH_2$— or —$CH(R_{12})CH_2$—O—$CH_2CH(R_{12})$—, wherein $R_{12}$ is an alkyl having 1-4 carbon atoms, and $A_4$ is oxygen or sulfur.

In another aspect, the present invention provides a method for preparing the compound of formula 7a by cyclocondensing a compound of the following formula 5 and a compound of the following formula 6:

[Formula 7a]

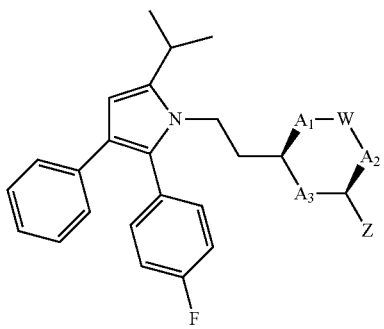

[Formula 5]

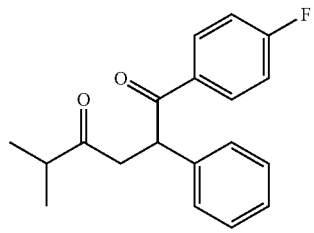

[Formula 6]

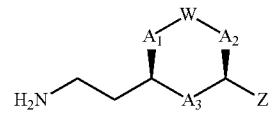

wherein $A_1$ and $A_2$ are oxygen;
$A_3$ is $CH_2$;
W is

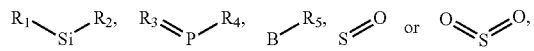

wherein $R_1$ and $R_2$ are each independently hydrogen, OH, a straight or branched chain alkyl having 1-8 carbon atoms, or phenyl, or $R_1$ and $R_2$ together form oxygen (=O) or —$(CH_2)_n$—, wherein n is 4 or 5, $R_3$ is oxygen or sulfur, $R_4$ is Cl, Br, F, I, a straight or branched chain having 1-8 carbon atoms, phenyl, trityl, OH, an alkoxy having 1-8 carbon atoms, or phenoxy, and $R_5$ is oxygen (=O), a straight or branched chain alkyl having 1-8 carbon atoms, an alkoxy having 1-8 carbon atoms, an aryl or aryloxy, wherein an aryl or aryloxy is unsubstituted or substituted with an alkyl having 1-4 carbon atoms, an alkoxy having 1-4 carbon atoms, nitro or halogen, or a $C_6$-$C_{10}$ heteroaryl comprising one or two heteroatoms selected from a group consisting of N, O and S; and
Z is —$CH_2COR_8$, wherein $R_8$ is

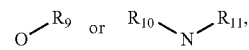

$R_9$ is hydrogen, a straight or branched chain alkyl having 1-8 carbon atoms, a cycloalkyl group having 3-6 carbon atoms, phenyl, benzyl or α,α-dimethylbenzyl, and $R_{10}$ and $R_{11}$ are each independently hydrogen, a straight or branched chain alkyl having 1-8 carbon atoms, a cycloalkyl group having 3-6 carbon atoms, benzyl or phenyl, or $R_{10}$ and $R_{11}$ together form —$(CH_2)_4$—, —$(CH_2)_5$—, —$(CH(R_{12})CH_2)_3$—, —$(CH(R_{12})CH_2)_4$—, —$(CH(R_{12})(CH_2)_2CH(R_{12}))$—, —$(CH(R_{12})(CH_2)_3CH(R_{12}))$—, —$CH_2CH_2$—O—$CH_2CH_2$—, —$CH(R_{12})CH_2$—O—$CH_2CH_2$— or —$CH(R_{12})CH_2$—O—$CH_2CH(R_{12})$—, wherein $R_{12}$ is an alkyl having 1-4 carbon atoms.

Advantageous Effects

According to the present invention, there is provided a method capable of producing a large amount of atorvastatin at high purity and high yield under mild reaction conditions.

MODE FOR INVENTION

The present invention relates to a method of preparing a compound of formula 1 at high efficiency and high yield using a compound of formula 7 and a compound of formula 8, which are key intermediates.

Also, the present invention relates to a compound of formula 7a, which is a novel intermediate, and to a preparation method thereof.

Specifically, the present invention relates to a method for preparing a compound of formula 1 or a pharmaceutically acceptable salt thereof, which comprises the steps of:

(1) reacting a compound of the following formula 7 with a compound of the following formula 8 to obtain a compound of the following formula 9, and (2) deprotecting and hydrolyzing the compound of formula 9:

[Formula 1]

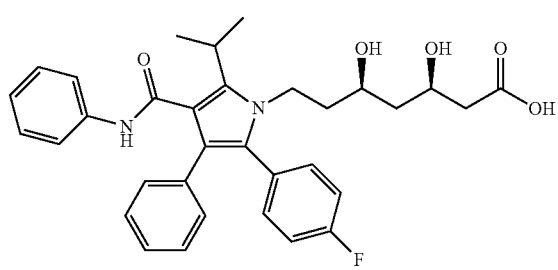

[Formula 7]

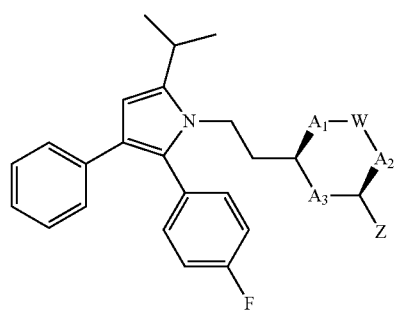

[Formula 8]

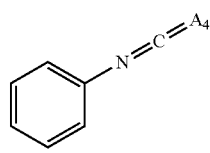

[Formula 9]

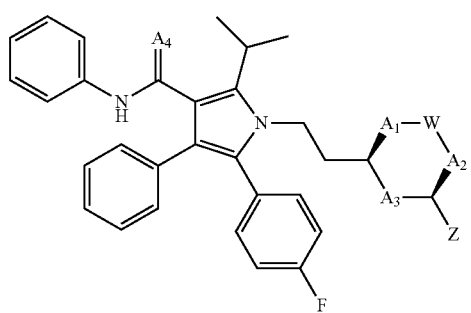

wherein $A_1$, $A_2$, $A_3$, $A_4$, W and Z are as defined above.

Preferably, when $A_1$ and $A_2$ are oxygen; $A_3$ is $CH_2$; $A_4$ is oxygen; W is

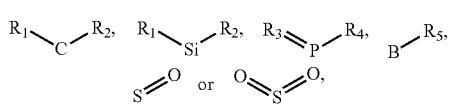

wherein $R_1$ and $R_2$ are dependently hydrogen, OH, methyl, ethyl, t-butyl, isopropyl or phenyl, or $R_1$ and $R_2$ together form oxygen (=O) or —$(CH_2)_n$—, wherein n is 4 or 5, $R_3$ is oxygen or sulfur, $R_4$ is Cl, Br, F, I, methyl, ethyl, t-butyl, isopropyl, trityl, phenyl, OH, methoxy, ethoxy or phenoxy, and $R_5$ is oxygen (=O), methyl, ethyl, t-butyl, isopropyl, methoxy, ethoxy, phenoxy, t-butoxy, phenyl, naphthalenyl, methoxyphenyl, ethoxyphenyl, nitrophenyl, difluorophenyl or quinolinyl; and Z is —$CH_2COR_8$, wherein $R_8$ is

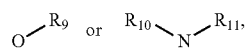

$R_9$ is hydrogen, methyl, ethyl, isopropyl, t-butyl, cyclohexyl, phenyl, benzyl or α,α-dimethylbenzyl, and $R_{10}$ and $R_{11}$ are each independently hydrogen, methyl, ethyl, t-butyl, isopropyl, cyclohexyl, benzyl or phenyl, or $R_{10}$ and $R_{11}$ together form —$(CH_2)_4$—, —$(CH_2)_5$—, —$(CH(R_{12})CH_2)_3$—, —$(CH(R_{12})CH_2)_4$—, —$(CH(R_{12})(CH_2)_2CH(R_{12}))$—, —$(CH(R_{12})(CH_2)_3CH(R_{12}))$—, —$CH_2CH_2$—O—$CH_2CH_2$—, —$CH(R_{12})CH_2$—O—$CH_2CH_2$— or $CH(R_{12})CH_2$—O—$CH_2CH(R_{12})$—, wherein $R_{12}$ is an alkyl having 1-4 carbon atoms.

When $A_1$ and $A_2$ are $CH_2$, $A_3$ is oxygen; $A_4$ is oxygen; W is

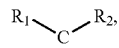

wherein $R_1$ is hydrogen, $R_2$ is

wherein $R_6$ is hydrogen, benzyl, trimethylsilyl, t-butyldimethylsilyl or t-butyldiphenylsilyl; and Z is oxygen (=O) or

wherein $R_7$ is hydrogen, methyl or ethyl.

More specifically, the present invention relates to a method of preparing the compound of formula 1 or a pharmaceutically acceptable salt thereof by using compounds of the following formula 9a and formula 9b:

[Formula 9a]

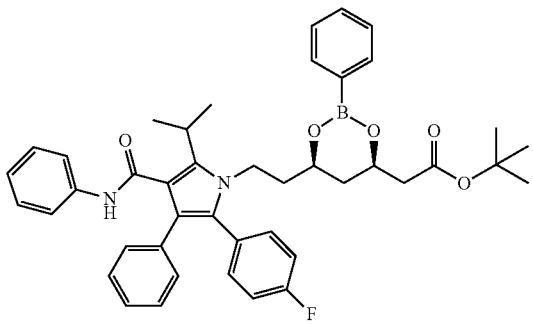

-continued

[Formula 9b]

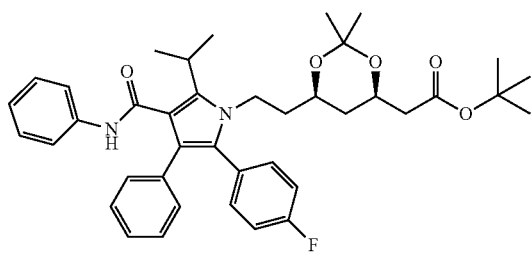

More specifically, in the reaction step (1), the compound of formula 9 can be prepared by reaching the compound of formula 7 with the compound of formula 8 in the presence of a selected reaction solvent and a selected acid.

In the step (1), the compound of formula 8 can be used in 1-10 molar equivalents, preferably 1-8 molar equivalents, and most preferably 2-6 molar equivalents. The reaction solvent is one or more selected from the group consisting of: halogen solvents, such as methylene chloride, chloroform, and carbon tetrachloride, aromatic solvents, such as toluene, benzene, nitrobenzene and xylene, and ether solvents, such as tetrahydrofuran, diethylether, dioxane and diisopropylether. The solvent is preferably a halogen solvent or an aromatic solvent, and most preferably methylene chloride.

As a selected acid, Lewis acid, preferably aluminum chloride, zinc chloride, trifluoroborane, tribromoborane, titanium tetrachloride, iron chloride or tin tetrachloride, and most preferably aluminum chloride is used. Herein, aluminum chloride is used in 1-10 molar equivalents, preferably 1-8 molar equivalents, and more preferably 2-6 molar equivalents. The reaction temperature is in the range from −78° C. to room temperature, preferably from −78° C. to 0° C., and most preferably from −78° C. to −40° C. The reaction time is between 10 minutes and 48 hours, and preferably between 10 minutes and 8 hours.

Meanwhile, in case that $A_4$ in the compound of formula 8 is sulfur, the compound of formula 9 can be prepared by carrying out the reaction between peroxide, such as m-chloroperoxybenzoic acid (m-CPBA) and hydrogen peroxide ($H_2O_2$) and the compound of formula 8, in a solvent selected from the group consisting of halogen solvents, such as methylene chloride and chloroform, alcoholic solvents, such as methanol and ethanol, and ether solvents, such as dioxane and tetrahydrofuran.

The reaction step (2) of synthesizing the compound of formula 1 by deprotecting and hydrolyzing the obtained compound of formula 9 can be carried out according to any method known in the art (see WO 02/057274), and the compound of formula 1 can be converted to a pharmaceutically acceptable salt thereof through a salt formation step.

Pharmaceutically acceptable salts include organic salts and inorganic salts. Preferred examples of organic salts include, but are not limited to, morpholine, piperazine, trimethylamine, triethylamine, dimethylamine, diethylamine, dipropylamine, diisopropylamine, dibenzylamine, dicyclohexylamine, lysine, ornitine, threonine, arginine, metformin, N-benzyl-2-phenylethanamine, 2-amino-2-methyl-1-propanol, 1-phenylethanamine, 1,2-ethanediamine, ammonia, 2-methyl-2-propanamine, phenethylamine and 2-(3,4-dimethoxyphenyl)ethanamine, and preferred examples of inorganic salts include, but are not limited to, alkali metals, such as lithium, sodium, potassium and cesium, alkaline earth metals, such as magnesium and calcium, aluminum, bismuth and iron.

The deprotection and/or hydrolysis reaction may be carried out by using alkali metal, preferably lithium hydroxide, sodium hydroxide, sodium bicarbonate, sodium carbonate, potassium bicarbonate, potassium carbonate or potassium hydroxide, and most preferably sodium hydroxide. Herein, sodium hydroxide can be used in 1-10 molar equivalents, preferably 3-7 molar equivalents, and most preferably 4-5 molar equivalents. The reaction temperature is 0-100° C., and preferably 0-50° C., and the reaction time is about 1-6 hours, and preferably about 2-4 hours.

A solvent, which is used in the reaction of step (2), is one or more selected from the group consisting of, for example, alcoholic solvents, such as methanol, ethanol, propanol or butanol, ether solvents, such as tetrahydrofuran, diethylether, dioxane or diisopropylether, and water. Preferably, a mixture of an ether solvent and water is used, and more preferably, a mixture of tetrahydrofuran and water is used.

The hydrolysis reaction may be carried out at the same time as the deprotection reaction, and a calcium salt formation reaction may be carried out without a separate purification process.

After the above-described deprotection and hydrolysis reactions conducted by using sodium hydroxide, a compound in the form of sodium salt is collected, and may then be prepared into atorvastatin hemicalcium salt in a selected solvent by using any one selected from the group consisting of calcium carbonate, calcium hydroxide, calcium acetate, calcium sulfate and calcium chloride. The equivalent of calcium acetate for the formation of calcium salt is preferably 0.5 mole.

The solvent that is used in the salt formation reaction is one or more selected from the group consisting of, for example, alcoholic solvents, such as methanol, ethanol, propanol or butanol, ether solvents, such as tetrahydrofuran, diethylether, dioxane or diisopropylether, and water. The solvent is preferably is a mixture of an alcoholic solvent and water, and more preferably a mixture of methanol and water.

The reaction temperature is 10-80° C., and preferably 10-60° C., and the reaction temperature is about 1-6 hours, and preferably about 1-3 hours.

Also, the present invention relates to a compound of the following formula 7a, which is a novel intermediate, and a preparation method thereof:

[Formula 7a]

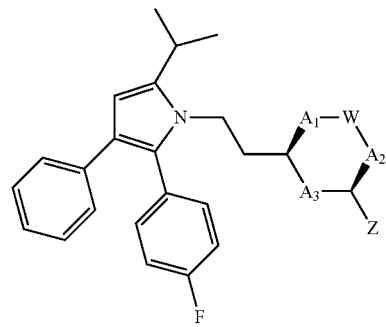

wherein $A_1$, $A_2$, $A_3$, W and Z are as defined above.

Preferably, $A_1$ and $A_2$ are oxygen; $A_3$ are $CH_2$; W is $$R_1\diagdown_{Si}\diagup R_2, \quad R_3\diagup\!\!\!\!=_P\diagup R_4, \quad _B\diagup R_5, \quad _S\!\!=\!\!{}^O \quad or \quad O\!\!=\!\!_S\!\!=\!\!{}^O,$$

wherein $R_1$ and $R_2$ are independently hydrogen, OH, methyl, ethyl, t-butyl, isopropyl or phenyl, or $R_1$ and $R_2$ together form oxygen (=O) or —$(CH_2)_n$—, wherein n is 4 or 5, $R_3$ is oxygen or sulfur, $R_4$ is Cl, Br, F, I, methyl, ethyl, t-butyl, isopropyl, trityl, phenyl, OH, methoxy, ethoxy or phenoxy, and $R_5$ is oxygen (=O), methyl, ethyl, t-butyl, isopropyl, methoxy, ethoxy, phenoxy, t-butoxy, phenyl, naphthalenyl, methoxyphenyl, ethoxyphenyl, nitrophenyl, difluorophenyl or quinolinyl; and Z is —$CH_2COR_8$, wherein $R_8$ is

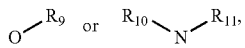

$R_9$ is hydrogen, methyl, ethyl, isopropyl, t-butyl, cyclohexyl, phenyl, benzyl or α,α-dimethylbenzyl, and $R_{10}$ and $R_{11}$ are each independently hydrogen, methyl, ethyl, t-butyl, isopropyl, cyclohexyl, benzyl or phenyl, or $R_{10}$ and $R_{11}$ together form —$(CH_2)_4$—, —$(CH_2)_5$—, —$(CH(R_{12})CH_2)_3$—, —$(CH(R_{12})CH_2)_4$—, —$(CH(R_{12})(CH_2)_2CH(R_{12}))$—, —$(CH(R_{12})(CH_2)_3CH(R_{12}))$—, —$CH_2CH_2$—O—$CH_2CH_2$—, —$CH(R_{12})CH_2$—O—$CH_2CH_2$— or —$CH(R_{12})CH_2$—O—$CH_2CH(R_{12})$—, wherein $R_{12}$ is an alkyl having 1-4 carbon atoms.

Most preferably, the compound of formula 7a is a compound of the following formula 7b:

[Formula 7b]

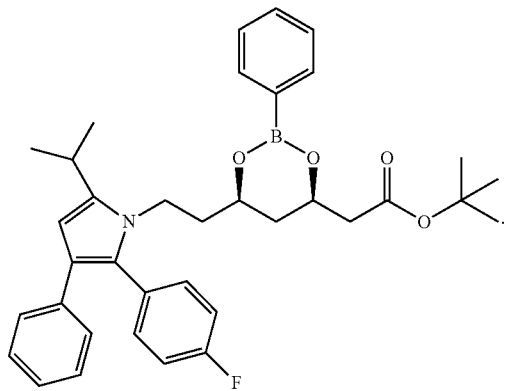

In the present invention, the compound of formula 7a can be prepared by cyclocondensing a compound of the following formula 5 and a compound of the following formula 6.

[Formula 7a]

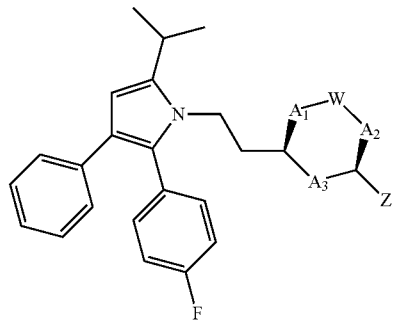

[Formula 5]

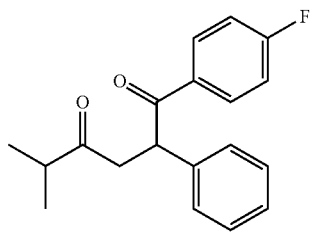

[Formula 6]

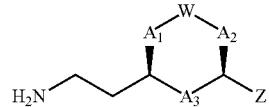

wherein $A_1$, $A_2$, $A_3$, W and Z are as defined above.

In the preparation method, the condensation of the compound of formula 5 with the compound of formula 6 is carried out in a selected organic solvent in the presence of acid to prepare the compound of formula 7a, and a water removal agent or a water removal device may be used to remove water during the reaction.

The organic solvent that is used in the reaction is one or more selected from the group consisting of hydrocarbon solvents, such as hexane, cyclohexane or heptane, aromatic solvents, such as toluene, benzene or xylene, ether solvents, such as tetrahydrofuran, diethylether, dioxane or diisopropylether, alcoholic solvents, such as methanol, ethanol, propanol or butanol, and polar solvents, such as dimethylformamide or N,N-dimethylacetamide. The solvent is preferably an aromatic solvent, and most preferably toluene.

The acid is pivalic acid, trifluoromethylsulfonic acid, methanesulfonic acid, p-toluenesulfonic acid or acetic acid, and preferably pivalic acid. The water removal agent may be molecular sieve, anhydrous magnesium sulfate or anhydrous sodium sulfate, and the water removal device may be a Dean-Stark trap. In the present invention, the Dean-Stark trap is preferably used to remove water.

In the cyclocondensation reaction, the reaction temperature is 50-110° C., preferably a reflux temperature suitable for the solvent, and more preferably 80-100° C. If the reaction temperature is low or exceeds 110° C., the reaction does not occur or byproducts are produced, leading to a significant decrease in the yield of the reaction. The reaction time is about 1-48 hours, preferably 5-30 hours, and more preferably 10-20 hours. Herein, the compound of formula 6 may be used in 1-3 molar equivalents, and preferably 1-1.5 molar equivalents.

In the preparation method of the present invention, the known compound of formula 5 can be obtained according to any method known in the art (see J. Med. Chem., 1991, 34, 357-366, and U.S. Pat. No. 5,003,081). Also, the known compound of formula 6 can be obtained according to the methods known in U.S. Pat. No. 5,003,081, and International Publication Nos. WO 05/012246, WO 03/070733, WO 89/07598 and WO 94/20492.

For example, according to the following reaction scheme 5, the compound of formula 5 can be prepared by subjecting a compound of formula 2 to a Knoevenagel condensation reaction with benzaldehyde in a n-hexane solvent in the presence of beta-alanine and acetic acid using a Dean-Stark trap, to prepare a compound of formula 3, subjecting the compound of formula 3 to a Stetter reaction with 4-fluorobenzaldehyde in reflux conditions in an ethanol solvent in the presence of a thiazolium catalyst to prepare a compound of formula 4, and subjecting the compound of formula 4 to decarboxylation in tetrahydrofuran in the presence of sodium hydroxide.

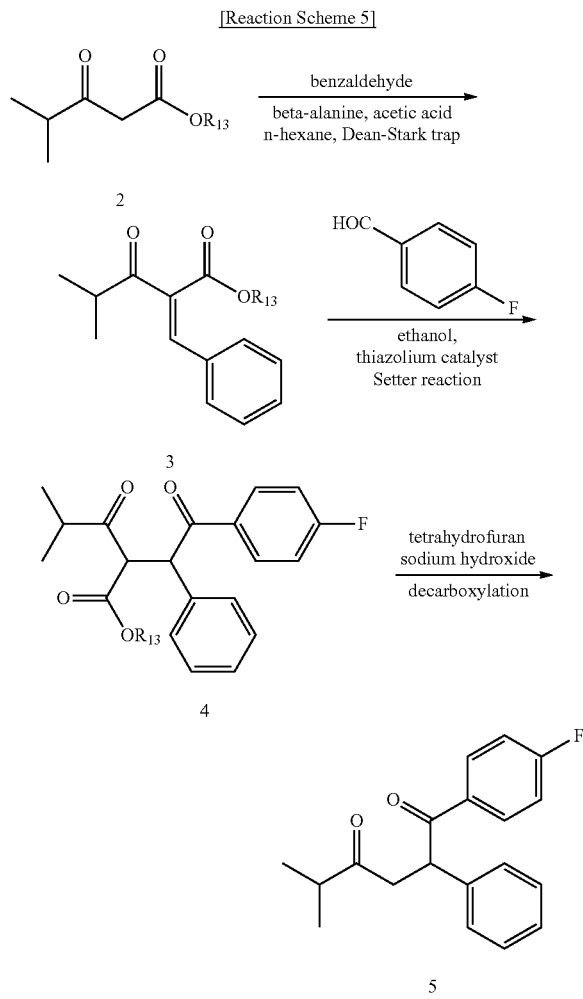

where $R_{13}$ is methyl or ethyl.

Hereinafter, the present invention will be described in further detail with reference to examples, but the scope of the present invention is not limited by these examples.

EXAMPLE 1

Preparation of methyl 4-methyl-3-oxo-2-(phenylmethylene)pentanoate 100 g of isobutylacetate was added to 1.5 L of hexane, and 6.2 g of beta-alanine, 63 ml of benzaldehyde and 22 ml of glacial acetic acid were added thereto with stirring in a nitrogen atmosphere. The resulting mixture was heated to reflux using a Dean-Stark trap for 20 hours to remove water. The reaction mixture was cooled to 20-25° C. and washed with 1.5 L of 1 N hydrochloric acid solution and 1.5 L of 10% sodium bicarbonate aqueous solution. The organic layer was separated, dried over anhydrous magnesium sulfate, filtered and concentrated under reduced pressure, thus obtaining 144 g of a geometric isomer mixture of methyl 4-methyl-3-oxo-2-(phenylmethylene)pentanoate as yellow oil.

$^1$H-NMR (400 MHz, CDCl$_3$) δ geometric isomer (isomer 1, 60%) 0.98 (d, J=6.8 Hz, 6H), 2.58 (m, 1H), 3.70 (s, 3H), 7.28 (m, 5H), 7.68 (s, 1H). (isomer 2, 40%) 1.14 (d, J=6.8 Hz, 6H), 3.14 (m, 1H), 3.70 (s, 3H), 7.80 (s, 5H), 7.48 (s, 1 H). MS (ESI) m/z 233.0 (M+1).

EXAMPLE 2

Preparation of (±)methyl-2-(2-(4-fluorophenyl)-2-oxo-1-phenylethyl)-4-methyl-3-oxopentanoate of [R-(R*,R*)], [R-(R*,S*)], [S-(R*,R*)] and [S-(R*,S*)] isomers To a solution of 31.4 g of 3-ethyl-5-(2-hydroxyethyl)-4-methylthiazolium bromide in 47 ml of anhydrous ethanol, 144 g of methyl 4-methyl-3-oxo-2-(phenylmethylene)pentanoate, 87 ml of triethanolamine and 74 ml of 4-fluorobenzaldehyde were added in an argon atmosphere. The resulting solution was stirred and heated at 70-80° C. for 20 hours. The reaction mixture was cooled to 20-25° C., and 2.0 L of ethyl acetate was added thereto. The resulting mixture was washed with 2.0 L of 1 N hydrochloric acid solution, 1.5 L of 10% sodium bicarbonate aqueous solution and 1.5 L of 10% sodium chloride aqueous solution. The organic layer was separated, dried over anhydrous magnesium sulfate, filtered and concentrated under reduced pressure, thus obtaining 206 g of (±)methyl 2-(2-(4-fluorophenyl)-2-oxo-1-phenylethyl)-4-methyl-3-oxopentanoate mixture of [R-(R*,R*)], [R-(R*, S*)], [S -(R*,R*)] and [S-(R*,S*)] isomers as yellow oil. In addition, the obtained oil compound was crystallized from ethanol, thus obtaining 198 g of the title compound as a light white solid.

$^1$H-NMR (400 MHz, CDCl$_3$) δ optical isomer (isomer 1, 95%) 1.01 (d, J=6.8 Hz, 3H), 1.26 (d, J=6.8 Hz, 3H), 2.92 (m, 1H), 3.51 (s, 3H), 4.72 (d, J=11.1 Hz, 1H), 5.32 (d, =11.1 Hz, 1H), 7.01-7.21 (m, 2H), 7.28-7.30 (m, 5H), 7.98-8.01 (m, 2H). (isomer 2, 5%) 0.52 (d, J=6.8 Hz, 3H), 0.89 (d, J=6.8 Hz, 3H), 2.29 (m, 1H), 3.70 (s, 3H), 4.73 (d, J=11.1 Hz, 1H), 5.32 (d, J=11.1 Hz, 1H), 7.01-7.21 (m, 2H), 7.21-7.27 (m, 5H), 7.98-8.01 (m, 2H). MS (ESI) m/z 357.2 (M+1).

EXAMPLE 3

Preparation of 1-(4-fluorophenyl)-5-methyl-2-phenyl-1,4-hexanedione (±)methyl 2-(2-(4-fluorophenyl)-2-oxo-1-phenylethyl)-4-methyl-3-oxopentanoate of [R-(R*,R*)], [R-(R*,S*)], [S-(R*,R*)] and [S-(R*,S*)] isomers, obtained in Example 2, was dissolved in 600 ml of tetrahydrofuran, and 300 mL of purified water and 41 g of sodium hydroxide were added to the mixture solution: The reaction solution was stirred at room temperature for 24 hours. 2.0 L of isopropylether was added to the reaction product to separate the organic layer, which was then dried over anhydrous magnesium sulfate, filtered and concentrated under reduced pressure, thus 141 g of the title compound as yellow oil.

$^1$H-NMR (400 MHz, CDCl$_3$) δ 1.08 (d, J=6.9 Hz, 3H), 1.13 (d, J=6.9 Hz, 3H), 2.65 (m, 1H), 2.77 (dd, J=3.8, 18.0 Hz, 1H), 3.63 (dd, J=10.2, 18.0 Hz, 1H), 5.07 (dd, J=3.8, 10.2 Hz, 1H), 7.10 (m, 2H), 7.27 (m, 5H), 7.98 (m, 2H). MS (ESI) m/z 299.0 (M+1).

EXAMPLE 4-1

Preparation of t-butyl 2-((4R,6R)-6-(2-(2-(4-fluorophenyl)-5-isopropyl-3-phenyl-1H-pyrrol-1-yl)ethyl)-2-phenyl-1,3,2-dioxaborinan-4-yl)acetate To a nitrogen-filled flask, 126 g of 1-(4-fluorophenyl)-5-methyl-2-phenyl-1,4-hexanedione, 2.5 L of toluene, 41 ml of triethylamine, 160 g of t-butyl 2-((4R,6R)-6-(2-aminoethyl)-2-phenyl-1,3,2-dioxaborinan-4-yl)acetate and 33 ml of pivalic acid were added. The mixture was heated to reflux with stirring for 14 hours while removing water with a Dean-Stark trap. The reaction mixture was cooled slowly to 20-25° C. and washed with purified water, and the organic layer was separated, dried over anhydrous magnesium sulfate, filtered, and concentrated under reduced pressure, thus obtaining 194 g of the title compound as yellow oil.

IR (KBr) 2922, 1761, 1740, 1600, 1515 cm$^{-1}$, $^1$H-NMR (400 MHz, CDCl$_3$) δ 1.32-1.39 (m, 7H), 1.53 (s, 9H), 1.59-1.73 (m, 2H), 1.84-1.87 (m, 1H), 2.39 (dd, J=15.2, 4.1 Hz, 1H), 2.55 (dd, 1H), 3.16 (m, 1H), 3.93-4.03 (m, 2H), 4.21-4.28 (m, 1H), 4.41-4.44 (m, 1H), 6.22 (s, 1H), 7.03-7.16 (m, 7H), 7.27-7.36 (m, 4H), 7.41-7.45 (m, 1H), 7.64-7.66 (d, J=6.8 Hz, 2H), MS (ESI) m/z 582.2 (M+1).

EXAMPLE 4-2

Preparation of t-butyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate According to the same method as described in Example 4-1, the title compound was synthesized using 1-(4-fluorophenyl)-5-methyl-2-phenyl-1,4-hexanedione and t-butyl 2-((4R,6R)-6-(2-aminoethyl)-2,2-dimethyl-1,3-dioxane-4-yl)acetate.

$^1$H-NMR (400 MHz, CDCl$_3$) δ 1.22-1.35 (m, 7H), 1.41-1.49 (m, 6H), 1.52 (s, 9H), 1.59-1.73 (m, 2H), 1.84-1.87 (m, 1H), 2.39-2.55 (m, 2H), 3.16 (m, 1H), 3.93-4.03 (m, 2H), 4.21-4.28 (m, 1H), 4.41-4.44 (m, 1H), 6.22 (s, 1H), 7.23-7.79 (m, 9H), MS (ESI) m/z 536.2 (M+1).

EXAMPLE 4-3

Preparation of 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetic acid According to the same method as in Example 4-1, the title compound was synthesized using 1-(4-fluorophenyl)-5-methyl-2-phenyl-1,4-hexanedione and 2-((4R,6R)-6-(2-aminoethyl)-2,2-dimethyl-1,3-dioxan-4-yl)acetic acid.

$^1$H-NMR (400 MHz, CDCl$_3$) δ 1.22-1.29 (m, 7H), 1.32-1.39 (m, 6H), 1.73-1.84 (m, 3H), 2.45 (m, 2H), 3.76 (m, 1H), 3.93-4.05 (m, 3H), 4.42 (m, 1H), 6.22 (s, 1H), 7.23-7.79 (m, 9H), MS (ESI) m/z 480.1 (M+1).

EXAMPLE 4-4

Preparation of ethyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate According to the same method as in Example 4-1, the title compound was synthesized using 1-(4-fluorophenyl)-5-methyl-2-phenyl-1,4-hexanedione and ethyl 2-((4R,6R)-6-(2-aminoethyl)-2,2-dimethyl-1,3-dioxan-4-yl)acetate.

$^1$H-NMR (400 MHz, CDCl$_3$) δ 1.02-1.29 (m, 10H), 1.41-1.49 (m, 6H), 1.59-1.73 (m, 2H), 1.84-1.87 (m, 1H), 2.39-2.55 (m, 2H), 3.16 (m, 1H), 3.93-4.03 (m, 2H), 4.21-4.28 (m, 3H), 4.41-4.44 (m, 1H), 6.22 (s, 1H), 7.23-7.79 (m, 9H), MS (ESI) m/z 508.0 (M+1).

EXAMPLE 4-5

Preparation of benzyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate According to the same method as in Example 4-1, the title compound was synthesized using 1-(4-fluorophenyl)-5-methyl-2-phenyl-1,4-hexanedione and benzyl 2-((4R,6R)-6-(2-aminoethyl)-2,2-dimethyl-1,3-dioxan-4-yl)acetate.

$^1$H-NMR (400 MHz, CDCl$_3$) δ 1.30-1.37 (m, 7H), 1.43-1.49 (m, 6H), 1.59-1.85 (m, 3H), 2.52-2.65 (m, 2H), 3.16 (m, 1H), 3.93-4.03 (m, 2H), 4.21-4.28 (m, 1H), 4.41-4.44 (m, 1H), 5.42 (s, 2H), 6.22 (s, 1H), 7.11-7.59 (m, 14H), MS (ESI) m/z 570.1 (M+1).

EXAMPLE 4-6

Preparation of 2-phenylpropan-2-yl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate According to the same method as in Example 4-1, the title compound was synthesized using 1-(4-fluorophenyl)-5-methyl-2-phenyl-1,4-hexanedione and 2-phenylpropan-2-yl 2-((4R,6R)-6-(2-aminoethyl)-2,2-dimethyl-1,3-dioxan-4-yl)acetate.

$^1$H-NMR (400 MHz, CDCl$_3$) δ 1.29-1.37 (m, 7H), 1.44-1.53 (m, 12H), 1.59-1.85 (m, 3H), 2.52-2.65 (m, 2H), 3.22 (m, 1H), 3.93-4.03 (m, 2H), 4.21-4.28 (m, 1H), 4.42-4.46 (m, 1H), 6.20 (s, 1H), 7.19-7.64 (m, 14H), MS (ESI) m/z 598.3 (M+1).

EXAMPLE 4-7

Preparation of t-butyl 2-((4R,6R)-6-(2-(2-(4-fluorophenyl)-5-isopropyl-3-phenyl-1H-pyrrol-1-yl)ethyl)-2-(3-nitrophenyl)-1,3,2-dioxaborinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-(3-nitrophenyl)-1,3,2-dioxaborinan-4-yl)acetate.

$^1$H-NMR (400 MHz, CDCl$_3$) δ 1.32-1.37 (m, 7H), 1.48 (s, 9H), 1.57-1.70 (m, 2H), 1.79-1.84 (m, 1H), 2.35 (m, 1H), 2.45-2.53 (m, 1H), 3.14-3.28 (m, 1H), 3.90-4.01 (m, 2H), 4.18-4.25 (m, 1H), 4.39-4.44 (m, 1H), 5.98 (s, 1H), 7.10-7.29 (m, 4H), 7.31-8.03 (m, 9H), MS (ESI) m/z 627.3 (M+1).

EXAMPLE 4-8

Preparation of t-butyl 2-((4R,6R)-6-(2-(2-(4-fluorophenyl)-5-isopropyl-3-phenyl-1H-pyrrol-1-yl)ethyl)-2-(4-methoxyphenyl)-1,3,2-dioxaborinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-(4-methoxyphenyl)-1,3,2-dioxaborinan-4-yl)acetate.

$^1$H-NMR (400 MHz, CDCl$_3$) δ 1.30-1.35 (m, 7H), 1.45 (s, 9H), 1.55-1.69 (m, 2H), 1.80 (m, 1H), 2.33-2.40 (m, 1H), 2.56 (m, 1H), 3.09-3.23 (m, 1H), 3.90-4.01 (m, 2H), 4.18-4.25 (m,

4H), 4.30-4.39 (m, 1H), 6.01 (s, 1H), 6.95-7.01 (m, 2H), 7.30-7.41 (m, 5H), 7.51-8.02 (m, 6H), MS (ESI) m/z 612.3 (M+1).

EXAMPLE 4-9

Preparation of t-butyl 2-((4R,6R)-2-ethyl-6-(2-(2-(4-fluorophenyl)-5-isopropyl-3-phenyl-1H-pyrrol-1-yl)ethyl)-1,3,2-dioxaborinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-ethyl-1,3,2-dioxaborinan-4-yl)acetate.

$^1$H-NMR (400 MHz, CDCl$_3$) δ 0.61 (q, J=7.2 Hz, 2H), 0.93 (t, J=7.2 Hz, 3H), 1.30-1.35 (m, 7H), 1.49 (s, 9H), 1.55-1.63 (m, 2H), 1.81-1.85 (m, 1H), 2.33 (m, 1H), 2.53 (m, 1H), 3.15-3.18 (m, 1H), 4.00 (m, 2H), 4.21-4.25 (m, 1H), 4.39-4.43 (m, 1H), 6.19 (s, 1H), 7.19-7.30 (m, 3H), 7.41-7.68 (m, 6H), MS (ESI) m/z 534.4 (M+1).

EXAMPLE 4-10

Preparation of t-butyl 2-((4R,6R)-6-(2-(2-(4-fluorophenyl)-5-isopropyl-3-phenyl-1H-pyrrol-1-yl)ethyl)-2-(methylphosphate)-1,3-dioxan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-methylphosphate-1,3-dioxan-4-yl)acetate.

$^1$H-NMR (400 MHz, CDCl$_3$) δ 1.30-1.36 (m, 7H), 1.45 (s, 9H), 1.55-1.63 (m, 2H), 1.77-1.82 (m, 1H), 2.33-2.56 (m, 2H), 3.08-3.17 (m, 1H), 3.91-4.00 (m, 5H), 4.21-4.26 (m, 1H), 4.34-4.40 (m, 1H), 6.03 (s, 1H), 7.20-7.31 (m, 4H), 7.39-7.59 (m, 5H), MS (ESI) m/z 572.3 (M+1).

EXAMPLE 4-11

Preparation of 1-(2-(4-(benzyloxy)-6-methoxytetrahydro-2H-pyran-2-yl)ethyl)-2-(4-fluorophenyl)-5-isopropyl-3-phenyl-1H-pyrrole According to the same method as in Example 4-1, the title compound was synthesized using 1-(4-fluorophenyl)-5-methyl-2-phenyl-1,4-hexanedione and 2-(4-(benzyloxy)-6-methoxytetrahydro-2H-pyran-2-yl)ethanamine.

$^1$H-NMR (400 MHz, CDCl$_3$) δ 1.26-1.31 (m, 6H), 1.50-1.53 (m, 1H), 1.74-1.81 (m, 2H), 1.88-1.92 (m, 3H), 2.80 (m, 1H), 3.38 (m, 1H), 3.48 (s, 3H), 3.61 (m, 1H), 3.86-3.89 (m, 2H), 4.80 (s, 2H), 4.91-4.93 (m, 1H), 6.39 (s, 1H), 7.13-7.49 (m, 12H), 7.62-7.69 (m, 2H), MS (ESI) m/z 528.7 (M+1).

EXAMPLE 4-12

Preparation of 4-(benzyloxy)-6-(2-(2-(4-fluorophenyl)-5-isopropyl-3-phenyl-1H-pyrrol-1-yl)ethyl)tetrahydro-2H-pyran-2-one According to the same method as in Example 4-1, the title compound was synthesized using 1-(4-fluorophenyl)-5-methyl-2-phenyl-1,4-hexanedione and 6-(2-aminoethyl)-4-(benzyloxy)tetrahydro-2H-pyran-2-one.

$^1$H-NMR (400 MHz, CDCl$_3$) δ 1.26-1.31 (m, 6H), 1.76-1.82 (m, 1H), 1.91-1.99 (m, 2H), 2.15-2.41 (m, 3H), 3.30-3.40 (m, 2H), 3.86-3.89 (m, 2H), 4.21 (m, 1H), 4.82 (s, 2H), 6.46 (s, 1H), 7.10-7.42 (m, 12H), 7.56-7.65 (m, 2H), MS (ESI) m/z 512.7 (M+1).

EXAMPLE 4-13

Preparation of t-butyl 2-((4R,6R)-2,2-di-t-butyl-6-(2-(2-(4-fluorophenyl)-5-isopropyl-3-phenyl-1H-pyrrol-1-yl)ethyl)-1,3,2-dioxasilinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2,2-di-t-butyl-1,3,2-dioxasilinan-4-yl)acetate.

$^1$H-NMR (400 MHz, CDCl$_3$) δ 0.99 (s, 18H), 1.29-1.38 (m, 7H), 1.53 (s, 9H), 1.56-1.65 (m, 2H), 1.84-1.8.8 (m, 1H), 2.43 (dd, J=15.0, 4.3 Hz, 1H), 2.58 (dd, J=15.2, 4.3 Hz, 1H), 3.16-3.18 (m, 1H), 3.85-3.92 (m, 2H), 4.18-4.20 (m, 1H), 4.29-4.33 (m, 1H), 6.31 (s, 1H), 7.13-7.28 (m, 7H), 7.62-7.69 (m, 2H), MS (ESI) m/z 636.9 (M+1).

EXAMPLE 4-14

Preparation of t-butyl 2-((4R,6R)-6-(2-(2-(4-fluorophenyl)-5-isopropyl-3-phenyl-1H-pyrrol-1-yl)ethyl)-2-(sulfite)-1,3-dioxan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-sulfite-1,3-dioxan-4-yl)acetate.

$^1$H-NMR (400 MHz, CDCl$_3$) δ 1.29-1.38 (m, 7H), 1.53 (s, 9H), 1.51-1.61 (m, 2H), 1.84-1.88 (m, 1H), 2.41 (dd, J=15.4, 4.1 Hz, 1H), 2.56 (dd, J=15.1, 4.3 Hz, 1H), 3.36-3.39 (m, 1H), 3.89-3.96 (m, 2H), 4.16-4.19 (m, 1H), 4.32-4.41 (m, 1H), 6.38 (s, 1H), 7.16-7.35 (m, 7H), 7.60-7.68 (m, 2H), MS (ESI) m/z 542.0 (M+1).

EXAMPLE 4-15

Preparation of ethyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According to the same method as in Example 4-1, the title compound was synthesized using 1-(4-fluorophenyl)-5-methyl-2-phenyl-1,4-hexanedione and ethyl 2-((2R,4R)-4-(2-aminoethyl)-1,5-dioxaspiro[5.5]undecan-2-yl)acetate.

$^1$H-NMR (400 MHz, CDCl$_3$) δ 1.12-1.16 (m, 3H), 1.22-1.35 (m, 6H), 1.41-1.49 (m, 6H), 1.59-1.73 (m, 5H), 1.84-1.87 (m, 4H), 2.39-2.55 (m, 2H), 3.16 (m, 1H), 3.93-4.03 (m, 1H), 4.03-4.14 (m, 2H), 4.21-4.28 (m, 1H), 4.41-4.44 (m, 1H), 6.22 (s, 1H), 7.23-7.79 (m, 9H), MS (ESI) m/z 548.3 (M+1).

EXAMPLE 4-16

Preparation of t-butyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According to the same method as in Example 4-1, the title compound was synthesized using 1-(4-fluorophenyl)-5-methyl-2-phenyl-1,4-hexanedione and t-butyl 2-((2R,4R)-4-(2-aminoethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.52 (s, 9H), 1.59-1.73 (m, 5H), 1.84-1.87 (m,

4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 9H), MS (ESI) m/z 576.3 (M+1).

EXAMPLE 4-17

Preparation of cyclohexyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According the same method as in Example 4-1, the title compound was synthesized using 1-(4-fluorophenyl)-5-methyl-2-phenyl-1,4-hexanedione and cyclohexyl 2-((2R,4R)-4-(2-aminoethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 12H), 1.59-1.73 (m, 9H), 1.84-1.87 (m, 4H), 2.39-2.55 (m, 2H), 3.16 (m, 1H), 3.78-3.86 (m, 1H), 3.93-4.03 (m, 1H), 4.21-4.28 (m, 1H), 4.41-4.44 (m, 1H), 6.22 (s, 1H), 7.23-7.79 (m, 9H), MS (ESI) m/z 602.3 (M+1).

EXAMPLE 4-18

Preparation of phenyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According to the same method as in Example 4-1, the title compound was synthesized using 1-(4-fluorophenyl)-5-methyl-2-phenyl-1,4-hexanedione and phenyl 2-((2R,4R)-4-(2-aminoethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 5H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 14H), MS (ESI) m/z 596.3 (M+1).

EXAMPLE 4-19

Preparation of benzyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According to the same method as in Example 4-1, the title compound was synthesized using 1-(4-fluorophenyl)-5-methyl-2-phenyl-1,4-hexanedione and benzyl 2-((2R,4R)-4-(2-aminoethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 5H), 1.84-1.87 (m, 41-1), 2.39-2.55 (m, 2H), 3.16 (m, 1H), 3.93-4.03 (m, 1H), 4.21-4.28 (m, 1H), 4.41-4.44 (m, 1H), 5.20-5.26 (m, 2H), 6.22 (s, 1H), 7.23-7.79 (m, 14H), MS (ESI) m/z 610.3 (M+1).

EXAMPLE 4-20

Preparation of 2-phenylpropan-2-yl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate According to the same method as in Example 4-1, the title compound was synthesized using 1-(4-fluorophenyl)-5-methyl-2-phenyl-1,4-hexanedione and 2-phenylpropan-2-yl 2-((2R,4R)-4-(2-aminoethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 11H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 14H), MS (ESI) m/z 638.3 (M+1).

EXAMPLE 4-21

Preparation of 2-((4R,6R)-6-(2-(2-(4-fluorophenyl)-5-isopropyl-3-phenyl-1H-pyrrol-1-yl)ethyl-2,2-dimethyl-1,3-dioxan-4-yl)-N,N-dimethylacetamide According to the same method as in Example 4-1, the title compound was synthesized using 1-(4-fluorophenyl)-5-methyl-2-phenyl-1,4-hexanedione and 2-((4R,6R)-6-(2-aminoethyl)-2,2-dimethyl-1,3-dioxan-4-yl)-N,N-dimethylacetamide.

$^1$H-NMR (400 MHz, CDCl$_3$) δ 1.28-1.48 (m, 13H), 1.73-1.90 (m, 3H), 2.18-2.43 (m, 2H), 2.9-3.0 (m, 6H), 3.12-3.14 (m, 1H), 3.79-4.02 (m, 4H) 6.26 (s, 1H), 7.03-7.48 (m, 9H), MS (ESI) m/z 507.2 (M+1).

EXAMPLE 4-22

Preparation of N,N-dicyclohexyl-2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetamide According to the same method as in Example 4-1, the tiotle compound was synthesized using 1-(4-fluorophenyl)-5-methyl-2-phenyl-1,4-hexanedione and 2-((4R,6R)-6-(2-aminoethyl)-2,2-dimethyl-1,3-dioxan-4-yl)-N,N-dicyclohexylacetamide.

$^1$H-NMR (400 MHz, CDCl$_3$) δ 1.25-1.42 (m, 16H), 1.44-1.53 (m, 13H), 1.73-1.94 (m, 7H), 2.22 (m, 1H), 2.43 (m, 1H), 3.1-3.54 (m, 3H), 3.79-4.03 (m, 4H), 6.27 (s, 1H), 7.03-7.49 (m, 9H), MS (ESI) m/z 643.2 (M+1)

EXAMPLE 4-23

Preparation of 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)-1-(piperidin-1-yl)ethanone According to the same method as in Example 4-1, the title compound was synthesized using 1-(4-fluorophenyl)-5-methyl-2-phenyl-1,4-hexanedione and 2-((4R,6R)-6-(2-aminoethyl)-2,2-dimethyl-1,3-dioxan-4-yl)-1-(piperidin-1-yl)ethanone.

$^1$H-NMR (400 MHz, CDCl$_3$) δ 1.24-1.41 (m, 12H), 1.48-1.52 (m, 7H), 1.73-1.95 (m, 3H), 2.15-2.44 (m, 2H), 3.12-3.34 (m, 5H), 3.78-4.02 (m, 4H), 5.61 (s, 1H), 7.01-7.47 (m, 9H), MS (ESI) m/z 547.0 (M+1)

EXAMPLE 4-24

Preparation of 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)-1-morpholinoethanone According to the same method as in Example 4-1, the title compound was synthesized using 1-(4-fluorophenyl)-5-methyl-2-phenyl-1,4-hexanedione and 2-((2R,4R)-4-(2-aminoethyl)-1,5-dioxaspiro[5.5]undecan-2-yl)-1-morpholinoethanone.

$^1$H-NMR (400 MHz, CDCl$_3$) δ 1.28-1.30 (m, 6H), 1.39-1.58 (m, 9H), 1.73-1.92 (m, 5H), 2.14-2.42 (m, 2H), 3.12-

3.22 (m, 1H), 3.41-3.67 (m, 8H), 3.68-4.10 (m, 4H), 6.25 (s, 1H), 7.01-7.45 (m, 9H), MS (ESI) m/z 589.0 (M+1)

EXAMPLE 4-25

Preparation of t-butyl 2-((4R,6R)-6-(2-(2-(4-fluorophenyl)-5-isopropyl-3-phenyl-1H-pyrrol-1-yl)ethyl)-2-methoxy-1,3,2-dioxaborinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-methoxy-1,3,2-dioxaborinan-4-yl)acetate.
$^1$H-NMR (400 MHz, CDCl$_3$) δ 1.30-1.35 (m, 7H), 1.49 (s, 9H), 1.54-1.63 (m, 2H), 1.81-1.86 (m, 1H), 2.33 (m, 1H), 2.53 (m, 1H), 3.15-3.18 (m, 1H), 4.00 (m, 2H), 4.12 (m, 3H), 4.21-4.25 (m, 1H), 4.39-4.43 (m, 1H), 6.20 (s, 1H), 7.19-7.31 (m, 3H), 7.40-7.66 (m, 6H), MS (ESI) m/z 536.0 (M+1).

EXAMPLE 4-26

Preparation of t-butyl 2-((4R,6R)-6-(2-(2-(4-fluorophenyl)-5-isopropyl-3-phenyl-1H-pyrrol-1-yl)ethyl)-2-(chloro)-1,3-dioxaphosphorinan-4-yl)acetate According to the same method as in Example 4-1, the title compound was synthesized using 1-(4-fluorophenyl)-5-methyl-2-phenyl-1,4-hexanedione and t-butyl 2-((4R,6R)-6-(2-aminoethyl)-2-chloro-1,3-dioxaphosphorinan-4-yl)acetate.
$^1$H-NMR (400 MHz, CDCl$_3$) δ 1.29-1.38 (m, 7H), 1.48 (s, 9H), 1.56-1.63 (m, 2H), 1.77-1.82 (m, 1H), 2.36-2.57 (m, 2H), 3.08-3.16 (m, 1H), 3.90-4.01 (m, 2H), 4.21-4.27 (m, 1H), 4.34-4.41 (m, 1H), 6.03 (s, 1H), 7.20-7.31 (m, 4H), 7.39-7.62 (m, 5H), MS (ESI) m/z 577.1 (M+1).

EXAMPLE 5-1

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-phenyl-1,3,2-dioxaborinan-4-yl)acetate 150 g of aluminum chloride and 1.5 L of methylene chloride were placed in a reactor in a nitrogen atmosphere and stirred. To the suspension, 121 ml of phenyl isocyanate was slowly added dropwise over 1 hour.

The reaction temperature was lowered to a temperature between −50° C. and −60° C., and a solution of 160 g of t-butyl 2-((4R,6R)-6-(2-(2-(4-fluorophenyl)-5-isopropyl-3-phenyl-1H-pyrrol-1-yl)ethyl)-2-phenyl-1,3,2-dioxaborinan-4-yl)acetate in 1.2 L of methylene chloride was slowly added dropwise to the reaction material over 1 hour and was then stirred for 1 hour. After the completion of the reaction, purified water was added to the reaction product, and the mixture was stirred for 30 minutes, heated slowly to room temperature, and then stirred for 30 minutes. The organic layer was separated three times with purified water and one time with a saturated aqueous sodium chloride solution. The organic layer was separated, dried over anhydrous magnesium sulfate, filtered, and concentrated under reduced pressure, thus obtaining oil. The oil was crystallized from isopropylether and heptane, thus obtaining 147 g of the title compound as a solid.
IR (KBr) 2916, 1741, 1662, 1598, 1507 cm$^{-1}$, $^1$H-NMR (400 MHz, DMSO-d$_6$) δ 1.35 (m, 6H), 1.40 (s, 9H), 1.47-1.97 (m, 4H), 2.36 (dd, J=15.0, 8.2 Hz, 1H), 2.52 (dd, J=15.0, 4.6 Hz, 1H), 3.29 (m, 1H), 3.96 (m, 1H), 4.14 (m, 2H), 4.40 (m, 1H), 6.93-7.52 (m, 19H), 9.83 (s, 1H), MS (ESI) m/z 701.0 (M+1).

EXAMPLE 5-2

The title compound as a light yellow solid was obtained in the same manner as in Example 5-1, except that zinc chloride was instead of aluminum chloride.

EXAMPLE 5-3

Preparation of t-butyl 2-((4R,6R)-6-(2-(2-(4-fluorophenyl)-5-isopropyl-3-phenyl-4-(phenylcarbamothioyl)-1H-pyrrol-1-yl)ethyl)-2-phenyl-1,3,2-dioxaborinan-4-yl)acetate The title compound was obtained in the same manner as in Example 5-1, except that phenylisothiocyanate was used instead of phenylisocyanate.
IR (KBr) 2912, 2181, 1761, 1662, 1600, 1507, 1211, 1024 cm$^{-1}$, $^1$H-NMR (400 MHz, DMSO-d$_6$) δ 1.34 (m, 6H), 1.39 (s, 9H), 1.51-1.98 (m, 4H), 2.35 (dd, J=15.0, 8.2 Hz, 1H), 2.54 (dd, J=15.0, 4.6 Hz, 1H), 3.31 (m, 1H), 3.93 (m, 1H), 4.13 (m, 2H), 4.40 (m, 1H), 6.89-7.52 (m, 19H), 10.59 (s, 1H), MS (ESI) m/z 717.1 (M+1).

EXAMPLE 5-4

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-phenyl-1,3,2-dioxaborinan-4-yl)acetate 2 g of t-butyl 2-((4R,6R)-6-(2-(2-(4-fluorophenyl)-5-isopropyl-3-phenyl-4-(phenylcarbamothioyl)-1H-pyrrol-1-yl)ethyl)-2-phenyl-1,3,2-dioxaborinan-4-yl)acetate obtained in Example 5-3 was dissolved in 70 ml of ethanol, and 0.83 g of sodium hydroxide and 35 ml of 30% hydrogen peroxide were added thereto. The mixture was stirred at room temperature for 3 hours. 300 ml of ethyl acetate and 200 ml of purified water were added to the reaction mixture and stirred slowly for 30 minutes, and the organic layer was separated and washed one time with a saturated aqueous sodium chloride solution. The organic layer was separated, dried over anhydrous magnesium sulfate, filtered, and concentrated under reduced pressure, thus obtaining oil. The oil was crystallized from isopropylether and heptane, thus obtaining the target compound as a solid compound.

EXAMPLE 5-5

Preparation of t-butyl 2-((4R,6R)-6-(2-(2-(4-fluorophenyl)-5-isopropyl-3-phenyl-4-(phenylcarbomyl)-1H-pyrrol-1-yl)ethyl)-2,2-dimethyl-1,3-dioxan-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate.
$^1$H-NMR (400 MHz, DMSO-d$_6$) δ 1.38 (m, 12H), 1.42 (s, 9H), 1.53-1.78 (m, 3H), 1.84-1.87 (m, 1H), 2.15 (m, 1H), 2.85 (m, 1H), 3.29 (m, 1H), 3.98-4.11 (m, 3H), 4.32 (m, 1H), 7.01-7.79 (m, 14H), 9.65 (s, 1H), MS (ESI) m/z 655.1 (M+1).

EXAMPLE 5-6

Preparation of 2-((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)acetic acid According to the same method as in Example 5-1, the title compound was synthesized using 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetic acid.

$^1$H-NMR (400 MHz, DMSO-$d_6$) δ 1.32-1.47 (m, 12H), 1.57-1.78 (m, 3H), 1.84-1.87 (m, 1H), 2.25 (m, 1H), 2.85 (m, 1H), 3.33 (m, 1H), 3.98-4.13 (m, 3H), 4.32 (m, 1H), 7.01-7.79 (m, 14H), 9.65 (s, 1H), 10.57 (s, 1H), MS (ESI) m/z 599.0 (M+1).

EXAMPLE 5-7

Preparation of ethyl 2-((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)acetate According to the same method as in Example 5-1, the title compound was synthesized using ethyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate.

$^1$H-NMR (400 MHz, DMSO-$d_6$) δ 1.22-1.38 (m, 15H), 1.53-1.78 (m, 3H), 1.84-1.87 (m, 1H), 2.25 (m, 1H), 2.64 (m, 1H), 3.29 (m, 1H), 3.98-4.21 (m, 5H), 4.32 (m, 1H), 7.05-7.79 (m, 14H), 9.56 (s, 1H), MS (ESI) m/z 637.0 (M+1).

EXAMPLE 5-8

Preparation of benzyl 2-((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)acetate According to the same method as in Example 5-1, the title compound was synthesized using benzyl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate.

$^1$H-NMR (400 MHz, DMSO-$d_6$) δ 1.29-1.41 (m, 12H), 1.56-1.84 (m, 4H), 2.25 (m, 1H), 2.64 (m, 1H), 3.25 (m, 1H), 3.96-4.12 (m, 3H), 4.32 (m, 1H), 5.12 (s, 2H), 7.03-7.78 (m, 19H), 9.52 (s, 1H), MS (ESI) m/z 689.2 (M+1).

EXAMPLE 5-9

Preparation of 2-phenylpropan-2-yl 2-((4R,6R)-6-(2-(2-(4-fluorophenyl)-5-isopropyl-3-phenyl-4-(phenylcarbamoyl)-1H-pyrrol-1-yl)ethyl)-2,2-dimethyl-1,3-dioxan-4-yl)acetate According to the same method as in Example 5-1, the title compound was synthesized using 2-phenylpropan-2-yl 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetate.

$^1$H-NMR (400 MHz, DMSO-$d_6$) δ 1.25-1.79 (m, 22H), 2.23 (m, 1H), 2.63 (m, 1H), 3.25 (m, 1H), 3.92-4.13 (m, 3H), 4.32 (m, 1H), 7.11-7.85 (m, 19H), 9.61 (s, 1H), MS (ESI) m/z 717.0 (M+1).

EXAMPLE 5-10

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-(3-nitrophenyl)-1,3,2-dioxaborinan-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2-(3-nitrophenyl)-1,3,2-dioxaborinan-4-yl)acetate.

$^1$H-NMR (400 MHz, DMSO-$d_6$) δ 1.30-1.34 (m, 6H), 1.40 (s, 9H), 1.45-2.00 (m, 4H), 2.33-2.38 (m, 1H), 2.50-2.55 (m, 1H), 3.26-3.29 (m, 1H), 3.94-4.00 (m, 1H), 4.11-4.20 (m, 2H), 4.38-4.42 (m, 1H), 7.22-7.68 (m, 18H), 9.52 (s, 1H), MS (ESI) m/z 746.3 (M+1).

EXAMPLE 5-11

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-(4-methoxyphenyl)-1,3,2-dioxaborinan-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2-(4-methoxyphenyl)-1,3,2-dioxaborinan-4-yl)acetate.

$^1$H-NMR (400 MHz, DMSO-$d_6$) δ 1.32 (d, J=7.3 Hz, 6H), 1.39 (s, 9H), 1.43-2.19 (m, 4H), 2.32-2.37 (m, 1H), 2.49-2.54 (m, 1H), 3.22-3.28 (m, 1H), 3.82-4.01 (m, 4H), 4.12-4.18 (m, 2H), 4.37-4.42 (m, 1H), 6.99-7.05 (m, 2H), 7.20-7.82 (m, 16H), 9.32 (s, 1H), MS (ESI) m/z 731.3 (M+1).

EXAMPLE 5-12

Preparation of t-butyl 2-((4R,6R)-2-ethyl-6-(2-(2-(4-fluorophenyl)-5-isopropyl-3-phenyl-4-(phenylcarbamoyl)-1H-pyrrol-1-yl)ethyl)-1,3,2-dioxaborinan-4-yl)acetate According to the same method as in Example 5-1, the title compound was synthesized using t-butyl 2-((4R,6R)-2-ethyl-6-(2-(2-(4-fluorophenyl)-5-isopropyl-3-phenyl-1H-pyrrol-1-yl)ethyl)-2-(4-methoxyphenyl)-1,3,2-dioxaborinan-4-yl)acetate.

$^1$H-NMR (400 MHz, DMSO-$d_6$) δ 0.64 (q, J=7.2 Hz, 2H), 0.95 (t, J=7.2 Hz, 3H), 1.32 (d, J=7.3 Hz, 6H), 1.41 (s, 9H), 1.42-2.08 (m, 4H), 2.34-2.41 (m, 1H), 2.26-2.49 (m, 1H), 3.25-3.31 (m, 1H), 3.85-3.93 (m, 1H), 4.15-4.21 (m, 2H), 4.36-4.41 (m, 1H), 7.19-7.64 (m, 14H), 9.25 (s, 1H), MS (ESI) m/z 653.4 (M+1).

EXAMPLE 5-13

Preparation of t-butyl 2-((4R,6R)-6-(2)-(2-(4-fluorophenyl)-5-isopropyl-3-phenyl-4-(phenylcarbamoyl)-1H-pyrrol-1-yl)ethyl)-2methoxy-2-oxo-1,3,2-dioxaphosphinan-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2-methoxy-2-oxo-1,3,2-dioxaphosphinan-4-yl)acetate.

¹H-NMR (400 MHz, DMSO-d₆) δ 1.35 (d, J=7.3 Hz, 6H), 1.45 (s, 9H), 1.96-2.10 (m, 4H), 2.32-2.42 (m, 1H), 2.44-2.50 (m, 1H), 3.20-3.29 (m, 1H), 3.76-3.98 (m, 4H), 4.12-4.19 (m, 2H), 4.32-4.38 (m, 1H), 7.10-7.81 (m, 14H), 9.20 (s, 1H), MS (ESI) m/z 691.3 (M+1).

EXAMPLE 5-14

Preparation of 1-(2-(4-(benzyloxy)-6-methoxytetrahydro-2H-pyran-2-yl)ethyl)-5-(4-fluorophenyl)-2-isopropyl-N,4-diphenyl-1H-pyrrol-3-carboxamide According to the same method as in Example 5-1, the title compound was synthesized using 1-(2-(4-(benzyloxy)-6-methoxytetrahydro-2H-pyran-2-yl)ethyl)-2-(4-fluorophenyl)-5-isopropyl-3-phenyl-1H-pyrrole.

¹H-NMR (400 MHz, DMSO-d₆) δ 1.25-1.33 (m, 6H), 1.51-1.53 (m, 1H), 1.74-1.81 (m, 2H), 1.88-1.90 (m, 3H), 2.79-2.83 (m, 1H), 3.42-3.51 (m, 4H), 3.59-3.62 (m, 1H), 3.86-3.89 (m, 2H), 4.80 (s, 2H), 4.91-4.93 (m, 1H), 7.13-7.38 (m, 7H), 7.45-7.55 (m, 10), 7.62-7.69 (m, 2H), 9.56 (s, 1H), MS (ESI) m/z 647.7 (M+1).

EXAMPLE 5-15

Preparation of 1-(2-(4-(benzyloxy)-6-oxotetrahydro-2H-pyran-2-yl)ethyl)-5-(4-fluorophenyl)-2-isopropyl-N,4-diphenyl-1H-pyrrol-3-carboxamide According to the same method as in Example 5-1, the title compound was synthesized using 4-(benzyloxy)-6-(2-(2-(4-fluorophenyl)-5-isopropyl-3-phenyl-1H-pyrrol-1-yl)ethyl)tetrahydro-2H-pyran-2-one.

¹H-NMR (400 MHz, DMSO-d₆) δ 1.31-1.39 (m, 6H), 1.74-1.80 (m, 1H), 1.91-1.97 (m, 2H), 2.20-2.43 (m, 3H), 3.30-3.35 (m, 1H), 3.41-3.46 (m, 1H), 3.84-3.87 (m, 2H), 4.25 (m, 1H), 4.80 (s, 2H), 7.02-7.35 (m, 7H), 7.42-7.56 (m, 10H), 7.64-7.75 (m, 2H), 9.48 (s, 1H), MS (ESI) m/z 631.7 (M+1).

EXAMPLE 5-16

Preparation of phenyl 1-(2-((4R,6R)-6-(2-t-butoxy-2-oxoethyl)-2,2-di-t-butyl-1,3,2-dioxasilinan-4-yl)ethyl)-5-(4-fluorophenyl)-2-isopropyl-4-phenyl-1H-pyrrol-3-carboxylate According to the same method as in Example 5-1, the title compound was synthesized using t-butyl 2-((4R,6R)-2,2-di-t-butyl-6-(2-(2-(4-fluorophenyl)-5-isopropyl-3-phenyl-1H-pyrrol-1-yl)ethyl)-1,3,2-dioxasilinan-4-yl)acetate.

¹H-NMR (400 MHz, DMSO-d₆) δ 0.97 (s, 18H), 1.28-1.39 (m, 7H), 1.53 (s, 9H), 1.51-1.63 (m, 2H), 1.82-1.87 (m, 1H), 2.42 (dd, J=15.0, 4.3 Hz, 1H), 2.53 (dd, J=15.2, 4.3 Hz, 1H), 3.16-3.18 (m, 1H), 3.81-3.91 (m, 2H), 4.19-4.22 (m, 1H), 4.26-4.31 (m, 1H), 6.89-7.09 (m, 6H), 7.18-7.25 (m, 6H), 7.67-7.75 (m, 2H), 9.41 (s, 1H), MS (ESI) m/z 756.0 (M+1).

EXAMPLE 5-17

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-oxo-1,3,2-dioxathian-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2-oxo-1,3,2-dioxathian-4-yl)acetate.

¹H-NMR (400 MHz, DMSO-d₆) δ 1.29-1.38 (m, 7H), 1.53 (s, 9H), 1.51-1.61 (m, 2H), 1.84-1.88 (m, 1H), 2.41 (dd, J=15.3, 4.1 Hz, 1H), 2.56 (dd, J=15.2, 4.0 Hz, 1H), 3.36-3.40 (m, 1H), 3.89-3.96 (m, 2H), 4.16-4.19 (m, 1H), 4.32-4.41 (m, 1H), 6.89-7.09 (m, 6H), 7.18-7.25 (m, 6H), 7.67-7.75 (m, 2H), 9.67 (s, 1H), MS (ESI) m/z 661.2 (M+1).

EXAMPLE 5-18

Preparation of ethyl 2-((2R,4R)-4-(2-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using ethyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate.

¹H-NMR (400 MHz, CDCl₃) δ 1.12-1.16 (m, 3H), 1.22-1.35 (m, 6H), 1.41-1.49 (m, 6H), 1.59-1.73 (m, 5H), 1.84-1.87 (m, 4H), 2.39-2.55 (m, 2H), 3.16 (m, 1H), 3.93-4.03 (m, 1H), 4.03-4.14 (m, 2H), 4.21-4.28 (m, 1H), 4.41-4.44 (m, 1H), 6.22 (s, 1H), 7.23-7.79 (m, 14H), 9.21 (br, 1H), MS (ESI) m/z 548.3 (M+1).

EXAMPLE 5-19

Preparation of t-butyl 2-((2R,4R)-4-(2-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using t-butyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate.

¹H-NMR (400 MHz, CDCl₃) δ 1.22-1.35 (m, 6H), 1.41-1.49 (m, 6H), 1.52 (s, 9H), 1.59-1.73 (m, 5H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 14H), 9.21 (br, 1H), MS (ESI) m/z 695.3 (M+1).

EXAMPLE 5-20

Preparation of cyclohexyl 2-((2R,4R)-4-(2)-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using cyclohexyl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate.

¹H-NMR (400 MHz, CDCl₃) δ 1.22-1.35 (m, 6H), 1.41-1.49 (m, 12H), 1.59-1.73 (m, 9H), 1.84-1.87 (m, 4H), 2.39-2.55 (m, 2H), 3.16 (m, 1H), 3.78-3.86 (m, 1H), 3.93-4.03 (m, 1H), 4.21-4.28 (m, 1H), 4.41-4.44 (m, 1H), 6.22 (s, 1H), 7.23-7.79 (m, 14H), 9.21 (br, 1H), MS (ESI) m/z 721.4 (M+1).

EXAMPLE 5-21

Preparation of phenyl 2-((2R,4R)-4-(2-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using phenyl 2-((2R,4R)-4-(2-(2-

(4-fluorophenyl)-5-isopropyl-3-phenyl-1H-pyrrol-1-yl)ethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 5H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 19H), 9.21 (br, 1H), MS (ESI) m/z 715.3 (M+1).

EXAMPLE 5-22

Preparation of benzyl 2-((2R,4R)-4-(2-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using benzyl 2-((2R,4R)-4-(2-(2-(4-fluorophenyl)-5-isopropyl-3-phenyl-1,4-pyrrol-1-yl)ethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 5H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 5.20-5.26 (m, 2H), 6.22 (s, 1H), 7.23-7.79 (m, 19H), 9.21 (br, 1H), MS (ESI) m/z 729.4 (M+1).

EXAMPLE 5-23

Preparation of 2-phenylpropan-2-yl 2-((2R,4R)-4-(2-(2-(4-fluorophenyl)-5-isopropyl-3-phenyl-4-(phenylcarbamoyl)-1H-pyrrol-1-yl)ethyl)-1,5-dioxaspiro[5.5]undecan-2-yl)acetate According to the same method as in Example 5-1, the title compound was synthesized using 2-phenylpropan-2-yl 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)acetate.

$^1$H-NMR (400 MHz, CDCl$_3$) δ 1.22-1.35 (m, 6H), 1.41-1.49 (m, 6H), 1.59-1.73 (m, 11H), 1.84-1.87 (m, 4H), 2.39-2.55 (m, 2H), 3.16 (m, 1H), 3.93-4.03 (m, 1H), 4.21-4.28 (m, 1H), 4.41-4.44 (m, 1H), 6.22 (s, 1H), 7.23-7.79 (m, 19H), 9.21 (br, 1H), MS (ESI) m/z 757.4 (M+1).

EXAMPLE 5-24

Preparation of 1-(2-((4R,6R)-6-(2-(dimethylamino)-2-oxoethyl)-2,2-dimethyl-1,3-dioxan-4-yl)ethyl)-5-(4-fluoronhenyl)-2-isopropyl-N,4-diphenyl-1H-pyrrol-3-carboxamide According to the same method as in Example 5-1, the title compound was synthesized using 2-((4R,6R)-6-(2-(2-(4-fluorophenyl)-5-isopropyl-3-phenyl-1H-pyrrol-1-yl)ethyl-2,2-dimethyl-1,3-dioxan-4-yl)-N,N-dimethylacetamide:

$^1$H-NMR (400 MHz, DMSO-d$_6$) δ 1.27-1.50 (m, 13H), 1.71-1.92 (m, 3H), 2.16-2.45 (m, 2H), 2.89-2.94 (m, 6H), 3.10-3.12 (m, 1H), 3.77-4.04 (m, 4H), 7.01-7.64 (m, 14H), 9.11 (s, 1H), MS (ESI) m/z 626.1 (M+1)

EXAMPLE 5-25

Preparation of 1-(2-((4R,6R)-6-(2-(dicyclohexylamino)-2-oxoethyl)-2,2-dimethyl-1,3-dioxan-4-yl)ethyl)-5-(4-fluorophenyl)-2-isopropyl-N,4-diphenyl-1H-pyrrol-3-carboxamide According to the same method as in Example 5-1, the title compound was synthesized using N,N-dicyclohexyl-2-((4R,6R)-6-(2-(2-(4-fluorophenyl)-5-isopropyl-3-phenyl-1H-pyrrol-1-yl)ethyl)-2,2-dimethyl-1,3-dioxan-4-yl)acetamide.

$^1$H-NMR (400 MHz, DMSO-d$_6$) δ 1.24-1.40 (m, 16H), 1.45-1.56 (m, 13H), 1.71-1.95 (m, 7H), 2.18-2.45 (m, 2H), 3.15-3.55 (m, 3H), 3.72-4.05 (m, 4H), 7.00-7.65 (m, 14H), 9.12 (s, 1H), MS (ESI) m/z 763.0 (M+1).

EXAMPLE 5-26

Preparation of 1-(2-((4R,6R)-2,2-dimethyl-6-(2-oxo-2-(pyridin-1-yl)ethyl)-1,3-dioxan-4-yl)ethyl)-5-(4-fluorophenyl)-2-isopropyl-N,4-diphenyl-1H-pyrrol-3-carboxamide According to the same method as in Example 5-1, the title compound was synthesized using 2-((4R,6R)-6-(2-(2-(4-fluorophenyl)-5-isopropyl-3-phenyl-1H-pyrrol-1-yl)ethyl)-2,2-dimethyl-1,3-dioxan-4-yl)-1-(piperidin-1-yl)ethanone.

$^1$H-NMR (400 MHz, DMSO-d$_6$) δ 1.22-1.42 (m, 12H), 1.43-1.55 (m, 7H), 1.76 (m, 1H), 1.85 (m, 2H), 2.18-2.42 (m, 2H), 3.10-3.35 (m, 5H), 3.75-4.04 (m, 4H), 7.03-7.68 (m, 14H), 9.21 (s, 1H), MS (ESI) m/z 666.1 (M+1).

EXAMPLE 5-27

Preparation of 5-(4-fluorophenyl)-2-isopropyl-1-(2-((2R,4R)-4-(2-morpholino-2-oxoethyl)-1,5-dioxaspiro[5.5]undecan-2-yl)ethyl)-N,4-diphenyl-1H-pyrrol-3-carboxamide According to the same method as in Example 5-1, the title compound was synthesized using 2-((2R,4R)-4-(2-(2-(4-fluorophenyl)-5-isopropyl-3-phenyl-1H-pyrrol-1-yl)ethyl)-1,5-dioxaspiro[5.5]undecan-2-yl)-1-morpholinoethanone.

$^1$H-NMR (400 MHz, DMSO-d$_6$) δ 1.25-1.33 (m, 6H), 1.34-1.55 (m, 9H), 1.74-1.90 (m, 5H), 2.13-2.52 (m, 2H), 3.11-3.32 (m, 1H), 3.41-3.65 (m, 8H), 3.78-4.15 (m, 4H), 7.03-7.73 (m, 14H), 9.02 (s, 1H), MS (ESI) m/z 708.0 (M+1).

EXAMPLE 5-28

Preparation of t-butyl 2-((4R,6R)-6-(2-(2-(4-fluorophenyl)-5-isopropyl-3-phenyl-4-(phenylcarbamoyl)-1H-pyrrol-1-yl)ethyl)-2-methoxy-1,3,2-dioxaborinan-4-yl)acetate According to the same method as in Example 5-1, the title compound was synthesized using t-butyl 2-((4R,6R)-6-(2-(2-(4-fluorophenyl)-5-isopropyl-3-phenyl-1H-pyrrol-1-yl)ethyl)-2-methoxy-1,3,2-dioxaborinan-4-yl)acetate.

$^1$H-NMR (400 MHz, DMSO-d$_6$) δ 1.32 (d, J=7.3 Hz, 6H), 1.41 (s, 9H), 1.42-2.08 (m, 4H), 2.34-2.41 (m, 1H), 2.26-2.49 (m, 1H), 3.25-3.31 (m, 1H), 3.40 (s, 3H), 3.85-3.93 (m, 1H), 4.15-4.21 (m, 2H), 4.36-4.41 (m, 1H), 7.19-7.64 (m, 14H), 9.25 (s, 1H), MS (ESI) m/z 655.0 (M+1).

EXAMPLE 6

Preparation of (3R,5R)-7-(2-(4-fluorophenyl)-5-isopropyl-3-phenyl-4-f_phenylcarbamoyl)-1H-pyrrol-1-yl)-3,5-dihydroxyheptanoate sodium salt In a reactor, 288 g of t-butyl 2-((4R,6R)-6-(2-(2-(4-fluorophenyl)-5-isopropyl-3-phenyl-4-(phenylcarbamoyl)-1H-pyrrol-1-yl)ethyl)-2-phenyl-1,3,2-dioxaborinan-4-yl)acetate was dissolved in 2 L of tetrahydrofuran, and then 2 L of purified water and 74 g of sodium hydroxide were added thereto. The reaction mixture was stirred at room temperature for 3 hours, and then extracted by addition of 2 L of ethyl acetate. The organic layer was separated, dried over anhydrous sodium sulfate, filtered, and concentrated under reduced pressure, thus obtaining oil. The obtained oil was crystallized from heptane, thus obtaining 213 g of the title compound as a white solid.

EXAMPLE 7

Preparation of (3R,5R)-7-(2-(4-fluorophenyl)-5-isopropyl-3-phenyl-4-(phenylcarbamoyl)-1H-pyrrol-1-yl)-3,5-dihydroxyheptanoate hemicalcium salt In a reactor, 213 g of the atorvastatin sodium salt, obtained in Example 6, was mixed with 1.0 L of methanol and 6.0 L of purified water, and the solution was then heated to 50° C. Then, the heated solution was slowly added dropwise to a solution of 0.5 molar equivalents of calcium acetate in 0.6 L of water in another reactor. After the completion of the addition, the mixture was slowly cooled to 15° C. with stirring for 2 hours, and then was filtered. The resulting solid was washed with 2 L of purified water, and then dried in a vacuum at 50° C., thus obtaining 205 g of atorvastatin hemicalcium salt.

IR (KBr) 3406, 1651, 1600, 1565, 1510, 1441, 1412, 1316, 1222, 1154, 843, 752 cm$^{-1}$, $^1$H-NMR (400 MHz, DMSO-d$_6$) δ 1.23 (m, 1H), 1.36 (d, J=6.5 Hz, 6H), 1.38-1.63 (m, 3H), 1.99 (m, 1H), 2.12 (m, 1H), 3.17-4.05 (m, 7H), 6.96-7.27 (m, 12H), 7.51 (d, J=7.8 Hz, 2H), 9.85 (s, 1H), MS (ESI) m/z 559.2 (M+1).

The invention claimed is:

1. A compound of the following formula 7a:

[Formula 7a]

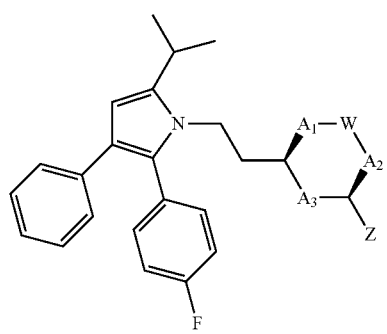

wherein $A_1$ and $A_2$ are oxygen;

$A_3$ is $CH_2$;

W is

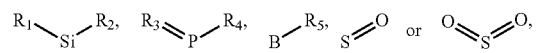

wherein $R_1$ and $R_2$ are each independently hydrogen, OH, a straight or branched chain alkyl having 1-8 carbon atoms, or phenyl, or $R_1$ and $R_2$ together form oxygen (=O) or —(CH$_2$)$_n$—, wherein n is 4 or 5, $R_3$ is oxygen or sulfur, $R_4$ is Cl, Br, F, I, a straight or branched chain having 1-8 carbon atoms, phenyl, trityl, OH, an alkoxy having 1-8 carbon atoms, or phenoxy, and $R_5$ is oxygen (=O), a straight or branched chain alkyl having 1-8 carbon atoms, an alkoxy having 1-8 carbon atoms, an aryl or aryloxy, wherein an aryl or aryloxy is unsubstituted or substituted with an alkyl having 1-4 carbon atoms, an alkoxy having 1-4 carbon atoms, nitro or halogen, or a C$_6$-C$_{10}$ heteroaryl comprising one or two heteroatoms selected from a group consisting of N, O and S; and Z is —CH$_2$COR$_8$, wherein $R_8$ is

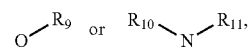

$R_9$ is hydrogen, a straight or branched chain alkyl having 1-8 carbon atoms, a cycloalkyl group having 3-6 carbon atoms, phenyl, benzyl or α,α-dimethylbenzyl, and $R_{10}$ and $R_{11}$ are each independently hydrogen, a straight or branched chain alkyl having 1-8 carbon atoms, a cycloalkyl group having 3-6 carbon atoms, benzyl or phenyl, or $R_{10}$ and $R_{11}$ together form —(CH$_2$)$_4$—, —(CH$_2$)$_5$—, —(CH(R$_{12}$)CH$_2$)$_3$—, —(CH(R$_{12}$)CH$_2$)$_4$—, —(CH(R$_{12}$)(CH$_2$)$_2$CH(R$_{12}$))—, —(CH(R$_{12}$)(CH$_2$)$_3$ CH(R$_{12}$))—, —CH$_2$CH$_2$—O—CH$_2$CH$_2$—, —CH(R$_{12}$)CH$_2$—O—CH$_2$CH$_2$— or —CH(R$_{12}$)CH$_2$—O—CH$_2$CH(R$_{12}$)—, wherein R$_{12}$ is an alkyl having 1-4 carbon atoms.

2. The compound of claim 1, which is a compound of the following formula 7a:

[Formula 7a]

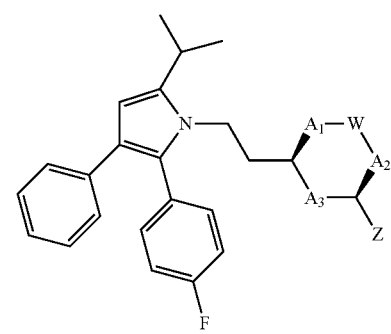

wherein $A_1$ and $A_2$ are oxygen;
$A_3$ is $CH_2$;
W is

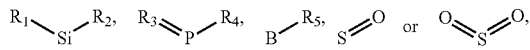

wherein $R_1$ and $R_2$ are each independently hydrogen, OH, methyl, ethyl, t-butyl, isopropyl or phenyl, or $R_1$ and $R_2$ together form oxygen (=O) or —(CH$_2$)$_n$—, wherein n is 4 or 5, $R_3$ is oxygen or sulfur, $R_4$ is Cl, Br, F, I, methyl, ethyl, t-butyl, isopropyl, trityl, phenyl, OH, methoxy, ethoxy or phenoxy, and $R_5$ is oxygen (=O), methyl, ethyl, t-butyl, isopropyl, methoxy, ethoxy, phenoxy, t-butoxy, phenyl, naphthalenyl, methoxyphenyl, ethoxyphenyl, nitrophenyl, difluorophenyl or quinolinyl; and Z is —CH$_2$COR$_8$, wherein R$_8$ is

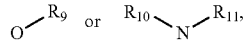

$R_9$ is hydrogen, methyl, ethyl, isopropyl, t-butyl, cyclohexyl, phenyl, benzyl or α,α-dimethylbenzyl, and $R_{10}$ and $R_{11}$ are each independently hydrogen, methyl, ethyl, t-butyl, isopropyl, cyclohexyl, benzyl or phenyl, or $R_{10}$ and $R_{11}$, together form —(CH$_2$)$_4$—, —(CH$_2$)$_5$—, —(CH(R$_{12}$)CH$_2$)$_3$—, —(CH(R$_{12}$)CH$_2$)$_4$—, —(CH(R$_{12}$)(CH$_2$)$_2$CH(R$_{12}$))—, —(CH(R$_{12}$)(CH$_2$)$_3$CH(R$_{12}$))—, —CH$_2$CH$_2$—O—CH$_2$CH$_2$—, —CH(R$_{12}$)CH$_2$—O—CH$_2$CH$_2$— or —CH(R$_{12}$)CH$_2$—O—CH$_2$CH(R$_{12}$)—, wherein $R_{12}$ is an alkyl having 1-4 carbon atoms.

3. The compound of claim 2, which is a compound of the following formula 7b:

[Formula 7b]

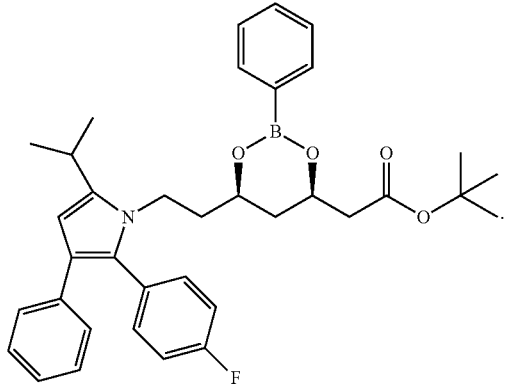

* * * * *

UNITED STATES PATENT AND TRADEMARK OFFICE
CERTIFICATE OF CORRECTION

PATENT NO.        : 8,178,697 B2
APPLICATION NO.   : 12/864139
DATED             : May 15, 2012
INVENTOR(S)       : Ahn et al.

It is certified that error appears in the above-identified patent and that said Letters Patent is hereby corrected as shown below:

The Inventors (75): Bong Kwan Soh, delete "(JP)" and insert -- (KR) --

Column 3, Line 50: Delete " 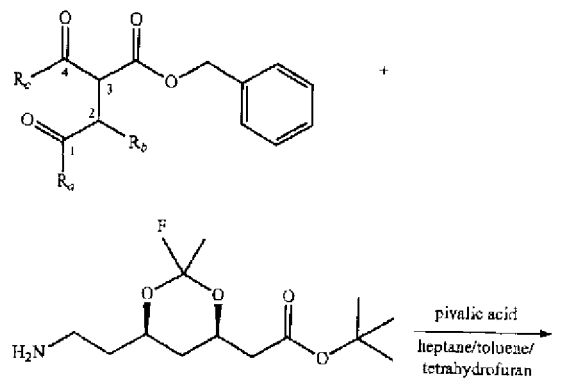 "

and insert -- 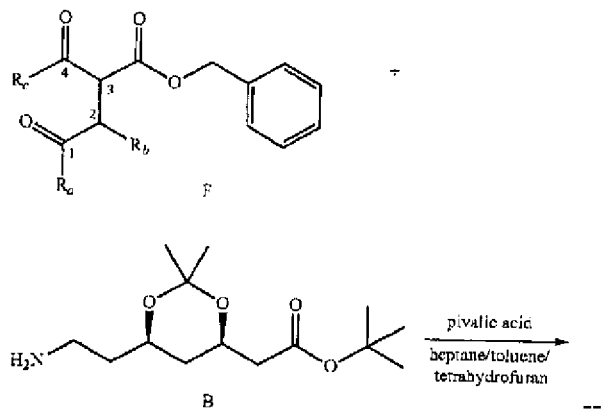 --

Signed and Sealed this
Seventh Day of August, 2012

David J. Kappos
*Director of the United States Patent and Trademark Office*

CERTIFICATE OF CORRECTION (continued)
U.S. Pat. No. 8,178,697 B2

Column 4, Line 60: Delete " 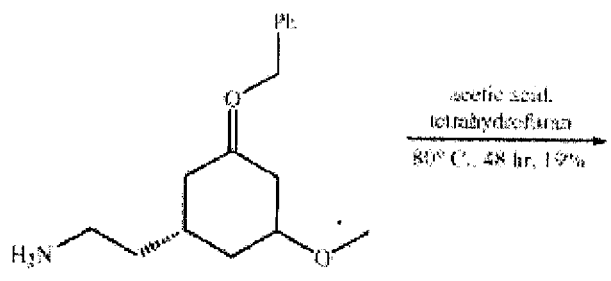 "

and insert -- 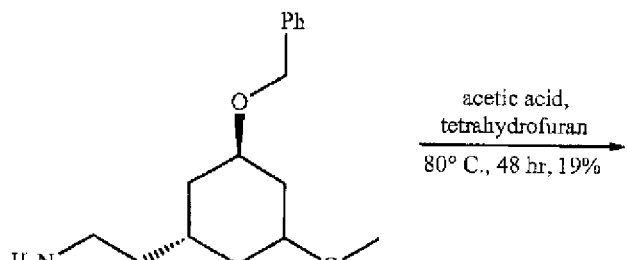 --

Column 18, Line 21: Delete "1H-pyrol" and insert -- 1H-pyrrol --

Column 24, Line 56: Delete "4-(phenylcarbomyl)-" and insert -- 4-(phenylcarbamoyl)- --

Column 26, Line 60: Delete "-2methoxy" and insert -- -2-methoxy --

Column 28, Line 43: Delete "2-((2R,4R)-4-(2)-(2-(4-" and insert -- 2-((2R,4R)-4-(2-(2-(4- --

Column 29, Line 56: Delete "(4-fluoronhenyl)" and insert -- (4-fluorophenyl) --

Column 31, Line 8: Delete "-4-f_phenylcarbamoyl)" and insert -- -4(phenylcarbamoyl) --